US012710422B2

(12) United States Patent
Arsene et al.

(10) Patent No.: US 12,710,422 B2
(45) Date of Patent: Aug. 18, 2026

(54) EXTRACELLULAR VESICLE CHARACTERIZATION SYSTEMS

(71) Applicant: Mursla Limited, London (GB)

(72) Inventors: Pierre Arsene, London (GB); Tomas Miguel De Freitas Dias, Cambridge (GB)

(73) Assignee: MURSLA LIMITED, London (GB)

(*) Notice: Subject to any disclaimer, the term of this patent is extended or adjusted under 35 U.S.C. 154(b) by 579 days.

(21) Appl. No.: 18/256,711

(22) PCT Filed: Dec. 7, 2021

(86) PCT No.: PCT/EP2021/084664
§ 371 (c)(1),
(2) Date: Jun. 9, 2023

(87) PCT Pub. No.: WO2022/122768
PCT Pub. Date: Jun. 16, 2022

(65) Prior Publication Data

US 2024/0044894 A1 Feb. 8, 2024

(30) Foreign Application Priority Data

Dec. 9, 2020 (GB) ..................................... 2019430

(51) Int. Cl.
*G01N 33/569* (2006.01)
*G01N 33/543* (2006.01)

(52) U.S. Cl.
CPC . *G01N 33/56966* (2013.01); *G01N 33/54346* (2013.01); *G01N 33/5438* (2013.01)

(58) Field of Classification Search
CPC ......... G01N 33/54346; G01N 33/5438; G01N 33/54386; G01N 33/56966; G01N 33/48; G01N 27/3278; G01N 27/44704; G01N 33/54326
See application file for complete search history.

(56) References Cited

FOREIGN PATENT DOCUMENTS

| | | | | |
|---|---|---|---|---|
| GB | 2573323 A | | 11/2019 | |
| GB | 2583550 A | * | 11/2020 | ......... G01N 33/5438 |
| WO | 2017032871 A1 | | 3/2017 | |
| WO | 2019211622 A1 | | 11/2019 | |

OTHER PUBLICATIONS

International Search Report and Written Opinion dated Mar. 14, 2022, for corresponding International Application No. PCT/EP2021/084664.

Chen et al. "Electrical Nanogap Devices for Biosensing" (2010) Materials Today, vol. 13, No. 11, pp. 28-41 doi:10.1016/s1369-7021(10)70201-7.

(Continued)

*Primary Examiner* — Ophelia A Hawthorne
(74) *Attorney, Agent, or Firm* — Renner Otto Boisselle & Sklar LLP; Christopher P. Harris

(57) ABSTRACT

A method of determining a number of epitopes on an exosome using a combination of optical and electrical interrogation techniques. Implementations of the method quantify the number of epitopes on a target exosome, e.g. a tumour-derived exosome.

34 Claims, 14 Drawing Sheets

(56) References Cited

OTHER PUBLICATIONS

Park et al. "High voltage-derived enhancement of electric conduction in nanogap devices for detection of prostate-specific antigen" (2010) Applied Physics Letters, 97(3), 033701 doi:10.1063/1.3464160.

Hoshino et al: "Extracellular vesicle and particle biomarkers define multiple human cancers", CelPress, Aug. 20, 2020, https://doi.org/10.1016/j.cell.2020.07.009, pp. 1044-1061.

K Rani et al: "A novel approach to correlate the salivary exosomes and their protein cargo in the progression of cognitive impairment into Alzheimer's disease", Cell (2020), J. Neuroscience Methods, vol. 347, 2021, pp. 1-5.

* cited by examiner 100
102
104
106
108
110
112
114
116
P 200
112
106
108
116

116
112
204
102
106
108
104

116
204
106

102
108
104
106
202

116
112
102
108
104
106
202

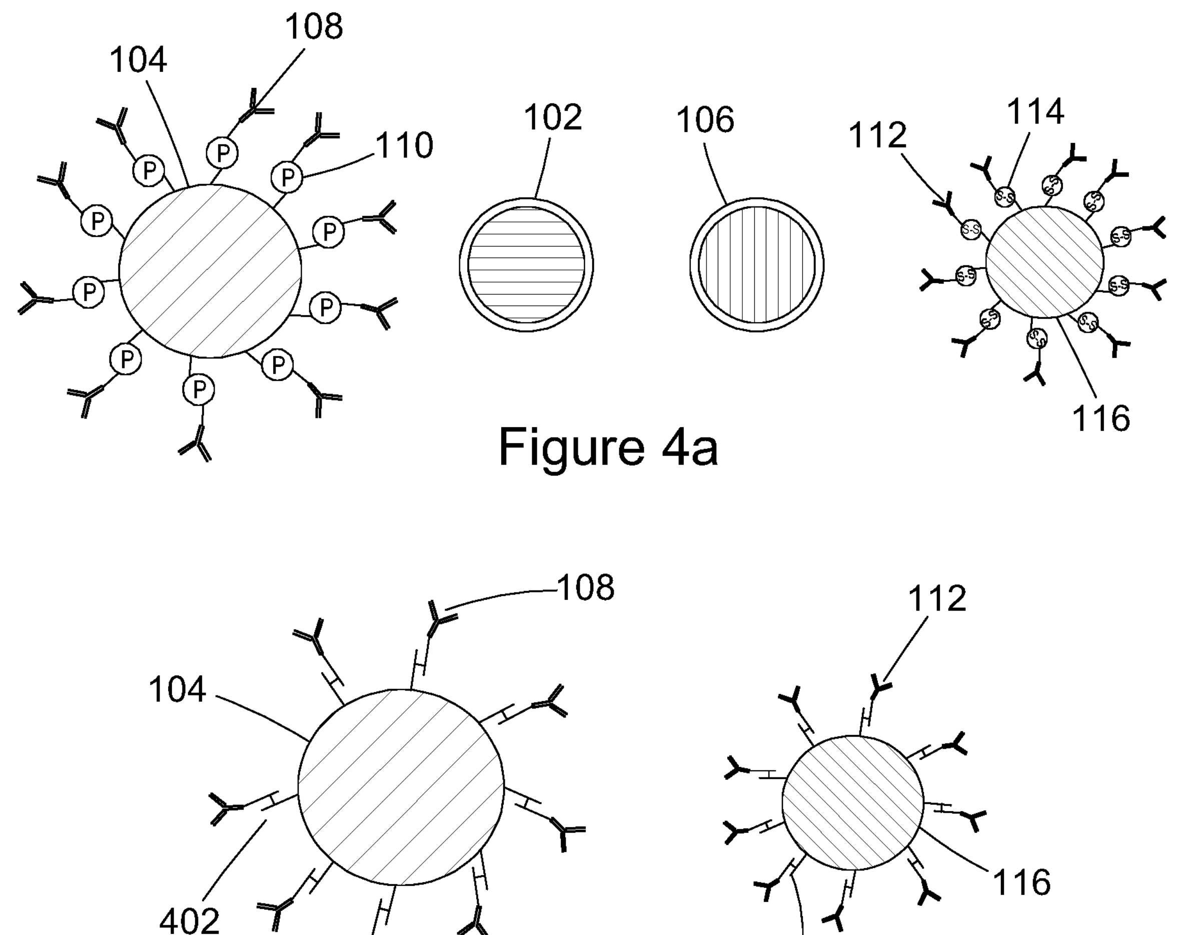
Figure 4a
Figure 4b
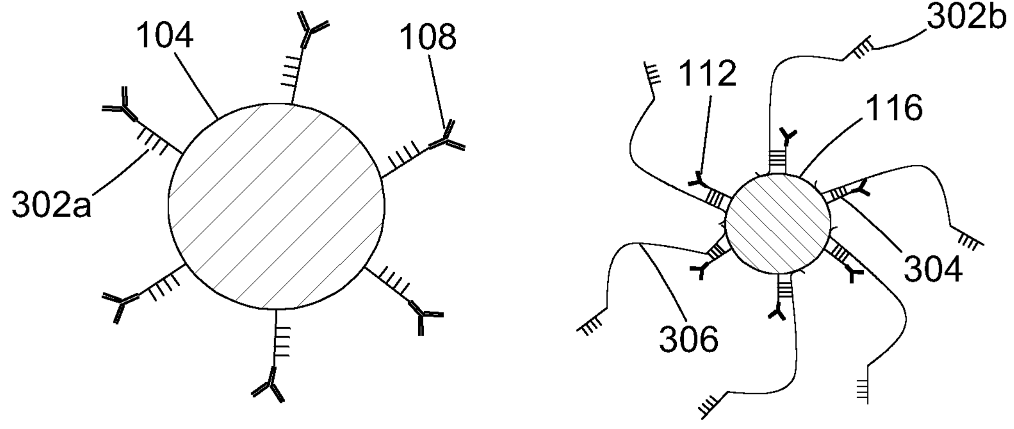
Figure 4c 102
106
104
116
1350
1306
1402
LYSING
1410
intensity
114
115
116
117
m/z
1420
RNA samples
cDNA
BRBL library
Sequencing
Whole Genome Expression Data

EXTRACELLULAR VESICLE CHARACTERIZATION SYSTEMS

RELATED APPLICATIONS

The present invention is a U.S. National Stage under 35 USC 371 patent application, claiming priority to PCT Application No. PCT/EP2021/084664, filed on Dec. 7, 2021, which claims priority from GB Patent Application No. 2019430.4 filed on Dec. 9, 2020; the entireties of both are hereby incorporated herein by reference.

FIELD

This specification relates to techniques for characterizing extracellular vesicles, for example exosomes.

BACKGROUND

Extracellular vesicles (EVs) such as exosomes can provide information on the cells from which they are released, but characterizing these is difficult. In WO2019/211622 (incorporated by reference) the inventors described techniques for detecting biological entities using closely spaced electrodes. Further background can be found in Hoshino et al., "Extracellular vesicle and particle biomarkers define multiple human cancers", Cell (2020), J. Neuroscience Methods, Vol 347, 2021, K Rani et al., "A novel approach to correlate the salivary exosomes and their protein cargo in the progression of cognitive impairment into Alzheimer's disease", WO2017/032871, and GB2573323.

SUMMARY

In one aspect there is described a method of determining a number of binding sites, in particular epitopes, on an extracellular vesicle. Implementations of the method quantify a number of epitopes of a target exosome, e.g. a tumour-derived exosome.

The method may comprise obtaining a liquid sample containing extracellular vesicles. The method may further comprise attaching electrically conducting nanoparticles to the extracellular vesicles. The method may further comprise attaching reporters to binding sites on the extracellular vesicles. The method may further comprise interrogating the reporters to determine a total number of bindings of the reporters to the extracellular vesicles. The method may further comprise determining a number of extracellular vesicles in the liquid sample by sensing an electrical response of the liquid sample using a pair of electrodes, in implementations separated by less than an average maximum dimension, e.g. an average diameter, of the electrically conducting nanoparticles, e.g. by a lateral distance of less than 200 nm. The method may further comprise combining the determined total number of bindings and the determined number of extracellular vesicles in the liquid sample to determine a number of binding sites per extracellular vesicle.

In some implementations a reporter may comprise a binding site recognition element, such as an antibody, aptamer, or lipid-binding protein.

In some implementations a binding site may be part of an antigen i.e. an epitope, and the method may thus determine a number of epitopes per extracellular vesicle. Then the reporter may comprise an antibody.

In implementations the nanoparticles are also attached to binding sites on the extracellular vesicles. These may be the same binding sites as those to which the reporters are attached, or different binding sites. In implementations an average dimension of the conducting nanoparticles is larger than an average dimension of the extracellular vesicles, to help limit a number of the conducting nanoparticles which may bind to an extracellular vesicle, e.g. to one. This is facilitated by attaching the extracellular vesicles to magnetic beads before attaching the conducting nanoparticles to the extracellular vesicles. In implementations the conducting nanoparticles are attached to the extracellular vesicles before the reporters are attached.

In some implementations two or more distinguishable type of reporters may be used, each with a different respective target binding site or epitope. In this way multiple different epitopes may be investigated in parallel. For example the number of binding sites or epitopes per extracellular vesicle may be estimated for each target binding site or epitope. The different types of reporters may be distinguishable by their different response on binding e.g. by their different optical response. For example the different types of reporters may be distinguishable by having optical responses at different respective wavelengths.

There is also described a corresponding system for determining a number of binding sites on an extracellular vesicle. The system may thus be configured to accept a liquid sample containing extracellular vesicles.

The system may be further configured to attach electrically conducting nanoparticles to the extracellular vesicles, e.g. via first binding site recognition elements; and to attach reporters to binding sites on the extracellular vesicles, e.g. via second binding site recognition elements (which may be the same as or different to the first binding site recognition elements). The system may be further configured to interrogate the reporters to determine a total number of bindings of the reporters to the extracellular vesicles, determine a number of extracellular vesicles in the liquid sample by sensing an electrical response of the liquid sample using a pair of electrodes, in implementations separated by less than an average maximum dimension e.g. an average diameter of the electrically conducting nanoparticles, or by a lateral distance of less than 200 nm. The system may be further configured to combine the determined total number of bindings and the determined number of extracellular vesicles in the liquid sample to determine number of binding sites per extracellular vesicle.

The system may also be configured to attach the extracellular vesicles to magnetic beads (in the liquid sample) before attaching the conducting nanoparticles to the extracellular vesicles. In implementations the magnetic beads have an average maximum dimension which is larger than the average maximum dimension, e.g. diameter, of the electrically conducting nanoparticles.

The ability to quantify binding sites such as epitopes can provide useful information on the extracellular vesicles. For example the overexpression of epitopes per EV may provide a biomarker of a disease such as cancer or a neurodegenerative disorder.

In another aspect a method of detecting or characterizing a number of binding sites on an extracellular vesicle comprises obtaining a liquid sample containing extracellular vesicles, attaching reporters to binding sites on the extracellular vesicles, and interrogating, e.g. optically interrogating, the reporters to characterize a number of bindings of the reporters to the extracellular vesicles. A corresponding system is also provided.

This approach is useful for detecting the presence of binding sites and can also be useful for approximately quantifying a number of binding sites e.g. for making a relative comparison. In some approaches the method includes amplification of a signal from the reporters.

Thus in another aspect a method of detecting or quantifying binding sites on an extracellular vesicle comprises obtaining a liquid sample containing extracellular vesicles; attaching reporters to binding sites on the extracellular vesicles; and interrogating the reporters to characterize a number of bindings of the reporters to the extracellular vesicles. Attaching reporters to binding sites on the extracellular vesicles may comprise attaching nanoparticles to the extracellular vesicles, wherein an average dimension of the nanoparticles is smaller than an average dimension of the extracellular vesicles, and attaching the reporters to the nanoparticles.

In each of the above described methods and systems by using reporters which selectively attach to binding sites the method/system may be used to detect and quantify multiple different binding sites or types of binding sites. For example the method may be repeated with the same liquid sample but different selectively attaching reporters; or different selectively attaching reporters may be used simultaneously.

The above described methods and systems can be used for detecting a disease in a biofluid sample which has previously been obtained from a human or animal patient. The biofluid may have previously been obtained non-invasively i.e. without intervention in a body of the patient e.g. from urine or breast milk. The biofluid sample may be used to obtain the liquid sample containing the extracellular vesicles, e.g. using conventional sample preparation techniques to remove contaminants in the sample.

FURTHER TECHNIQUES

Some implementations of the described methods and systems may be combined with features and aspects of the further techniques described below.

A method of isolating target extracellular vesicles, EVs, from a biofluid comprising a plurality of target EVs and non-target EVs. The method comprises: introducing a plurality of EV capture microparticles to the biofluid to obtain a precursor mixture, wherein the plurality of EV capture microparticles are functionalised, via a plurality of first linkers, with EV-specific binding agents specific to an EV surface marker, such that a plurality of bound microparticle-EV assemblies is formed in the precursor mixture; extracting the bound microparticle-EV assemblies to obtain a cleaned precursor mixture; introducing a plurality of target capture nanoparticles to obtain an assembly mixture, wherein the plurality of target capture nanoparticles are functionalised with target-specific binding agents receptive to surface markers comprised on the target EVs, such that the target capture nanoparticles bind to the plurality of target EV; and cleaving the plurality of first linkers to dissociate at least the plurality of target EVs from the EV capture microparticles. After the cleaving, the method further comprises extracting the plurality of EV capture microparticles and applying at least one of dielectrophoresis or centrifugation to extract the plurality of target capture nanoparticles, such that the target EVs are separated from the non-target EVs.

After the final separation step of target from non-target EVs by dielectrophoresis or centrifugation, the target EVs may still be bound to the target capture nanoparticles.

The target capture nanoparticles can be introduced either to the initial precursor mixture or to the cleaned precursor mixture; irrespective of the order, a clean solution free of contaminants is still formed as a result of the capture of EVs by the EV capture microparticles. The optional step of applying dielectrophoresis comprises the application of an alternating electric field, which acts upon the target capture nanoparticles. Thus, in examples, a dielectrophoretic force can be induced on the target capture nanoparticles such that the nanoparticles (and any target particles to which they are bound) are drawn towards, or repelled from, the origin of the alternating electrical field.

The method may further comprise, removing unbound target capture nanoparticles before the cleaving of the plurality of first linkers. In detail, after introducing the plurality of target capture nanoparticles, assemblies comprising EV capture microparticles, target capture nanoparticles, non-target EVs, and target EVs, are formed. However, some target capture nanoparticles may not have bound/captured to any target EVs (for example, if an excess of target capture nanoparticles is used.) Therefore, in some examples, any unbound target capture nanoparticles are desired to be removed before the step of cleaving the microparticles from the EVs. Removal/extraction of target capture nanoparticles prior to the cleaving step is advantageous in examples where bound target capture nanoparticles are subsequently used as the detection or quantification labels.

For example, the removal of the unbound target capture nanoparticles may comprise sequestering the above-mentioned assemblies and washing away any unbound target-capture nanoparticles. For example, in examples where the EV capture microparticles are magnetic, the assemblies comprising the microparticles (or microparticles) may be sequestered by a magnet, thus allowing free particles (including the unbound target capture nanoparticles) to be washed away.

The plurality of target capture nanoparticles may be functionalised with the target-specific binding agents, via a plurality of second linkers that are not cleaved during the step of cleaving the plurality of first linkers. Accordingly, the method may further comprise: after separating the plurality of target EVs from the non-target EVs, cleaving the plurality of second linkers to dissociate the plurality of target capture nanoparticles from the plurality of target EVs; and applying at least one of dielectrophoresis or centrifugation to extract the dissociated target capture nanoparticles and isolate a plurality of unbound target EVs. Isolated target EVs are thus available for downstream applications such as biomarker discovery, and the dissociated target capture nanoparticles may be counted separately in order to determine the precise number of specifically isolated EVs (as, beneficially, target capture nanoparticles become bound to target EVs in a substantially 1:1 ratio, meaning that the number of nanoparticles indicates the number of isolated EVs).

Therefore, it will be appreciated that, in some examples, the first and second linkers are responsive to different cleaving treatments, and cannot be cleaved using the same treatment. Specifically, the plurality of second linkers may comprise disulfide bonds, which are cleaved by treatment with a reducing or alkaline reagent. The plurality of first linkers may be photo-cleavable linkers, which are cleaved by exposure to UV or near-UV light. Beneficially, UV light does not cleave the disulfide bonds comprised in the second linkers.

The plurality of first linkers may alternatively comprise DNA or RNA, which are cleaved by treatment with an enzyme. For example, the enzyme may be a nuclease. At least one of the EV-specific binding agents used in any of the above examples, and the target-specific binding agent, may be an antibody. For example, the antibody may be receptive to antigens comprised on a surface of the EVs or the target EVs.

In an alternate example, the plurality of first linkers comprise DNA or RNA, and the plurality of target capture nanoparticles comprise a plurality of second linkers comprising DNA or RNA, where the method may further comprise: treating the assembly mixture with an enzyme to cleave a plurality of bound first linkers and a plurality of bound second linkers, the plurality of bound first and second linkers being bound to a target EV, to dissociate the plurality of target EVs from each of the EV capture microparticles and the target capture nanoparticles, such that the plurality of target EVs are separated from the plurality of non-target EVs. Advantageously, only a single cleaving step is required here, such that non-target EVs remain bound to the microparticles and can easily be extracted away from the target EVs. Furthermore, the plurality of second linkers may be terminated with two receptors: a first receptor bearing target-specific antibodies that are receptive to target-specific markers comprised on the target EVs; and a second receptor bearing additional DNA or RNA which is receptive to the DNA or RNA in the plurality of first linkers. In this example, the method may further comprise applying at least one of dielectrophoresis, or centrifugation, to extract the dissociated target capture nanoparticles, to isolate a plurality of unbound target EVs.

Generally, the above examples of the isolation method may comprise: introducing the plurality of unbound target EVs to a second plurality of the EV capture microparticles; introducing a second plurality of target capture nanoparticles functionalised with second target-specific binding agents receptive to surface markers comprised on a subset of the unbound target EVs; cleaving the plurality of first linkers on the second plurality of the EV capture microparticles and extracting said second plurality of EV capture microparticles; and applying at least one of dielectrophoresis or centrifugation to extract the second plurality of target capture nanoparticles and isolate the subset of the target EVs. Furthermore, a second cleavage step may again be performed in order to sever the linkers on the second plurality of target capture nanoparticles, in order to dissociate the subset of target EVs from the nanoparticles.

Advantageously, the use of a second plurality of the EV capture microparticles and a second plurality of target capture nanoparticles enables a further selection of EVs, so that a refined sub-population of EVs can be isolated. This is enabled by virtue of the fact that the isolation method keeps the EVs intact, such that an isolated population of EVs can be carried forward for a further round of isolation. In principle, multiple, even indefinite, rounds of isolation can be performed using increasingly specific target-markers on the target capture nanoparticles in order to obtain an ultra-refined set of target EVs.

The plurality of EV capture microparticles may be magnetic, wherein the steps of extracting the bound microparticle-EV assemblies and extracting the plurality of EV capture microparticles comprise applying a magnetic field.

The method may further comprise characterising the plurality of target EVs, the characterising comprising one or more of: polymerase chain reaction (PCR), mass spectrometry, DNA or RNA sequencing, and liquid chromatography. It may be advantageous to combine some of the above methods, for example, performing liquid chromatography and mass spectrometry in tandem. The plurality of unbound target EVs may be lysed prior to the characterisation, to release an internal EV content, such that the characterisation is performed on the internal EV content. In one embodiment, the internal EV content may be characterised to identify one or more disease-specific biomarkers. In a further example, it is has been found that EVs from virus-infected cells, such as SARS-CoV2 and other retroviruses, contain viral proteins and RNA cargo. Accordingly, in a further embodiment, the internal EV content may be characterised to identify the presence of viral proteins and/or RNA cargo. As such, the present method may enable the detection of a virus and/or the diagnosis of a viral infection by characterising EV content as described above.

In some examples, once the target EVs have been isolated from the non-target EVs, a step is performed to quantify the number of target particles present. Accordingly, each of the target EVs of the plurality of target EVs, having been separated from the non-target EVs, may be comprised in a bound EV-nanoparticle assembly, where the method further comprises: applying an electric field between a pair of electrodes to concentrate the bound EV-nanoparticle assembly in a sensing region, wherein the sensing region is defined by a region between the pair of electrodes, which are separated by a lateral distance of less than 100 nm; applying a nanoparticle sensing voltage between the electrodes; characterizing a response of the sensing region to the nanoparticle sensing voltage to determine EV quantification data; and quantifying a number of target EVs from the quantification data.

Preferably, a length dimension of the plurality of EV capture microparticles is about an order of magnitude greater (i.e. around ten times greater) than a length dimension of each of the target EVs, or about two orders of magnitude greater (i.e. around one hundred times greater) in terms of surface area, such that, in the plurality of bound microparticle-EV assemblies, no two target EVs are proximate when bound to a surface of the plurality of EV capture microparticles. Thus a microparticle may have an (average) minimum dimension e.g. diameter of at least 0.5, 1, or 2 μm.

The meaning of proximate will be understood to be a relative term, and generally means that target EVs are spread out over the surface of the, larger, microparticle. This has the result that all target EVs are separated, over the surface of the microparticles, by at least their own diameter. In examples, the EVs are separated by at least the size dimension of the target capture nanoparticles such that one target capture nanoparticle intercepts/captures just one target particle.

Each target capture nanoparticle of the plurality of target capture nanoparticles thus preferably captures at most one target EV. In more detail, in preferred examples, the result of relative sizes of the nanoparticles to the microparticles is a ratio of 1:1 of target EVs to nanoparticles in the bound target-nanoparticles assemblies. This provides advantages for quantification purposes, i.e., such that it can be reliably inferred that the number of nanoparticles sensed equates exactly to the number of target EVs present.

The plurality of target EVs may have a size (dimension) of around 20 nm to 160 nm, and the plurality of target EVs may be exosomes. Furthermore, all the EVs in a sample biofluid may be exosomes. In other words, the biofluid may contain only or substantially exosomes, wherein the target EVs are a sub-population of the exosomes in the biofluid. In this example, the sub-population may contain a surface marker representative of a particular disease and/or a particular organ or tissue of an organism. In other words, the exosome carries a cell-surface specific biomarker.

In some approaches there is a first isolation step where a population of exosomes are isolated from a biofluid, and a second step where a subset of the initially-isolated exosomes are isolated using a second set of target-capture nanoparticles. The target capture nanoparticles may be gold nanoparticles, functionalised with one or more specific binding agents that target a highly specific (i.e., disease or tissue specific) exosome surface marker. For example, the first isolation step may comprise isolating all exosomes. The second step may comprise isolating a target exosome from the exosome population, e.g. all exosomes carrying a target-specific marker. The target-specific marker may be a biomarker or a tissue-specific biomarker, e.g., from isolated brain-originating exosomes, all exosomes carrying a disease-specific marker which express a particular protein, merely for example, Amyloid Beta, amyloid precursor protein (APP), alpha-synuclein, close homolog of L1, insulin receptor substrate 1 (IRS-1), neural cell adhesion molecule (NCAM) and tau protein, or an exosome surface marker such as tetraspanin, such as CD9, CD63, CD81, CD326, CD82, CD37 or CD41; which may indicate presence of a neurodegenerative disorder.

The above described techniques are being able to isolate a highly specific subset of exosomes from a complex fluid containing a variety of EVs, where a proportion of the EVs are non-target exosomes and target exosomes. The complex biofluid may further contain contaminants such as peptides, protein aggregates, cell fragments, cholesterol lipoproteins, and the like. In particular, the biofluid may contain free-floating (i.e., not EV-bound) biomarkers or EV-bound biomarkers from organs/tissues other than the targeted organs/tissues, which are disregarded by the selection of tissue-specific markers (e.g. neuronal markers selection).

Generally, the biofluid may be obtained from a cell culture, or directly from a patient. For example, the sample may be any suitable body fluid, such as for example blood, urine, saliva, sputum or lymph cerebrospinal fluid.

The target capture nanoparticles may be gold nanoparticles. However, the target capture nanoparticles may also comprise silver, or generally any other conductive, e.g. metallic or semi-metallic, material. A size (dimension) of target capture nanoparticles may be around 50 nm to 300 nm, e.g. around 200 nm. In examples where target EVs are isolated for discovery purposes, the GNPs may be even smaller than 50 nm.

In general, an extracellular vesicle, EV, is a biological vesicle of around 20-160 nm size. Nevertheless, the isolation methods described above may also be carried out, using the equivalent steps, to isolate lipoproteins (i.e. low density lipoproteins and high-density lipoproteins, LDL and HDLs), and other biological entities having a lipid bilayer as a cell-membrane.

BRIEF DESCRIPTION OF THE DRAWINGS

Some aspects of the invention will now be further described by way of example only, with reference to the accompanying figures.

FIGS. 4*a*-4*c* show the individual nanoparticles and exosomes present in the isolation strategies illustrated in FIGS. 1-3.

In the Figures like elements are indicated by like reference numerals.

DETAILED DESCRIPTION

Figures 1A, 1B, 1C, 1D, 1E:
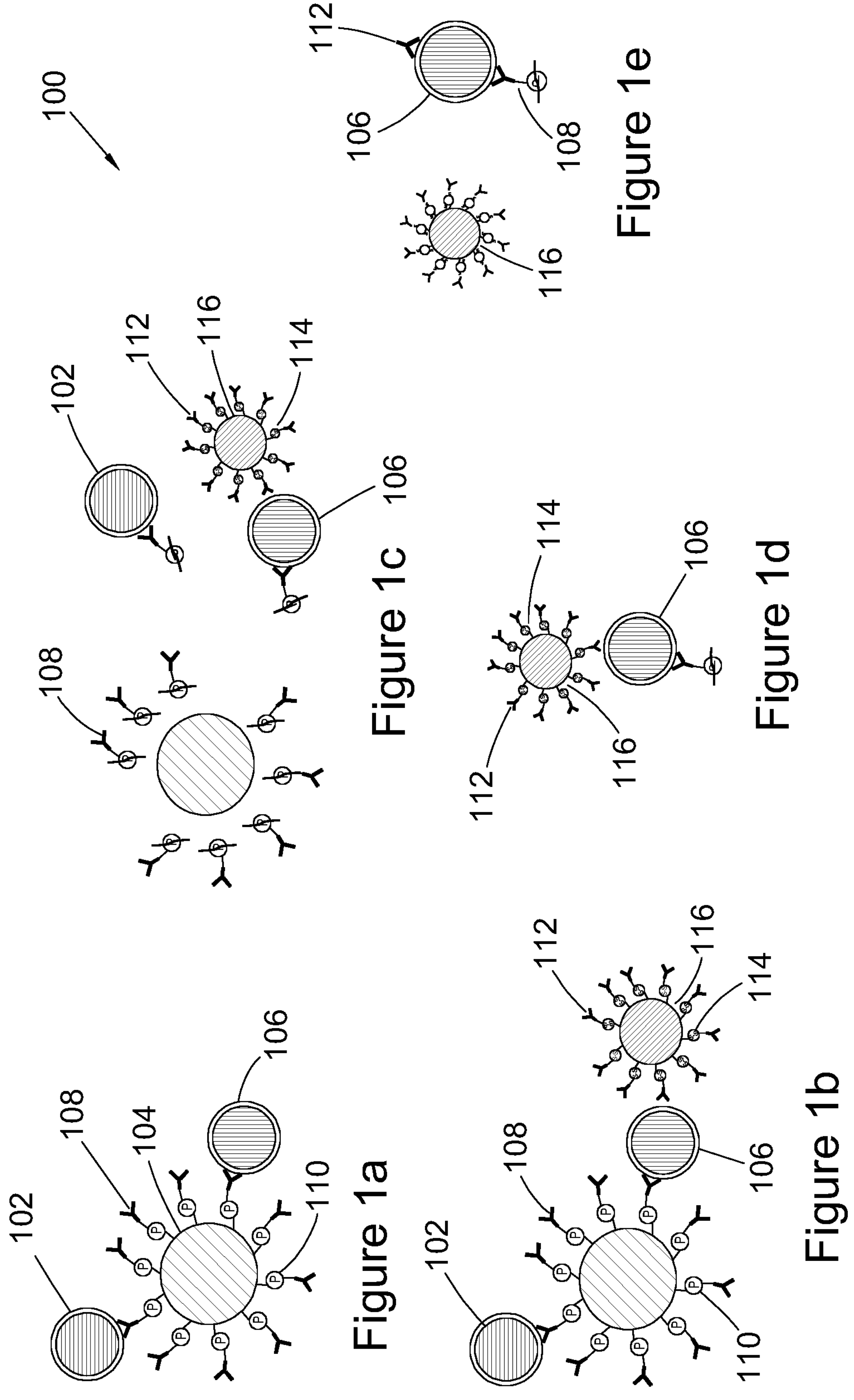
FIGS. 1*a*-1*e* show part of an example exosome isolation strategy using photo-cleavable linkages and disulfide linkages.

There are first described technical details helpful for understanding the invention.

Thus there is described a process for isolating sub-populations of extracellular vesicles (EVs) from biofluids or lab-based cell cultures. The EVs, when isolated, can be screened in applications such as biomarker discovery for identification of diseases or the identification of novel markers indicative of a particular disease. This also enables identification of new therapy targets, and for the identification of EVs with regenerative ability (e.g. Mesenchymal stem cell EVs).

Extracellular vesicle (EV) is a broad definition and generally includes Exosomes, Ectosomes and Microvesicles, amongst other biomolecules. EVs share the common characteristic of cell membranes formed of a lipid-bilayers, and they lack the ability to replicate. Commonly, within the family of EVs, exosomes are viewed as promising targets for the aforementioned discovery applications. Exosomes are membranous nanometer-sized vesicles (i.e. 40-160 nm) that are actively released by all known cells. During their biogenesis, they assimilate a variety of cellular content specific to their parent cells. Exosomes share many membrane-bound proteins at their surface. For example, tetraspanin proteins CD63, CD9 and CD81 are known examples that are commonly targeted as universal exosome biomarkers, present on the surface of exosomes. However, because all tissues are different and the cells that make those tissues express different material, exosomes also contain (typically internally) tissue-specific or cell-specific molecules such as RNAs and proteins. This is also true in diseased cells, where the diseased and aberrant cells may overexpress specific content that can be detected in or on exosomes.

The process includes at least two steps, which can in general be repeated:

In the first step EVs and/or exosomes are captured on μm-sized particles, preferably through antibody-based affinity, taking advantage of known exosome universal markers (for example, the above mentioned tetraspanins). This first step simultaneously cleans the biofluid from other particles, cell fragments, contaminants and free circulating proteins. The microparticles are preferably magnetic such that they can be extracted using a magnetic field. For example, a specific structure of a suitable microparticle is: a silicon core and covered with a polymer shell composed of highly cross-linked polystyrene; magnetic material (i.e., ferromagnetic material such as iron or nickel) is precipitated in pores distributed throughout the particle. The surface chemistry used to functionalise the microparticles to capturing/sequestering EVs depends on the polymer shell. Generally, the shell is usually hydrophilic which confers an ability to form covalent amide bonds with proteins.

In the second step, sub-populations of target-specific EVs bound to the microparticles used in the first step are captured or tagged with nanoparticles functionalised with target-specific binding agents. These binding agents can be antibodies specific to certain surface markers present only on a subpopulation of EVs. The desired subpopulation of EVs may be exosomes, or a specific family of exosomes, for example. Thus, an assembly of microparticles-EV-nanoparticle is formed. These assemblies can be dissociated such that only the exosomes-nanoparticles complexes are recovered, thus removing from solution the populations of non-target EVs bound to the microparticles.

Generally, this isolation method allows the capture of all EV/exosome populations based on universal markers, in addition to cleaning contaminants from the mixture such as freely circulating proteins, other extracellular vesicles or particles. Next, having captured a general population of EVs/exosomes, a sub-population of the general population is selected, based on a surface marker indicative of a specific tissue or disease in the second step. This enables accurate characterization of sub-populations of EVs/exosomes that would otherwise be difficult or impossible to capture using only one selection/capture step. In particular, having only a target-specific selection step would likely lead to the selection of any target surface marker freely circulating in the biofluid, rather than only on the surface of the EVs or exosomes. Once the target sub-population of EVs is isolated from non-targets using the above method, the target population is immediately available for analysis in subsequent assays, for example any from the group of: PCR, and in particular RT-PCR, RNA-Seq, ELISA, LC-MS-Chromatography, nanoparticle tracking, and the like. In one example, the EV may be lysed and the protein or nucleic acid content characterised. Such characterisation may involve determining the presence of one or more biomarkers within the EV. Alternatively, such characterisation may lead to the identification of one or more new EV biomarkers.

In implementations the nanoparticles are functionalised with more specific binding agents/antibodies than the microparticles. Therefore, the nanoparticles tag only a specific population of EVs bound to the microparticles, which can be retrieved by several methods such as centrifugation or dielectrophoresis and subsequently assessed, where other irrelevant EVs or exosomes are discarded. In this way, purified populations or sub-populations of EVs/exosomes bound to the nanoparticles are then dissociated and individually suitable for downstream characterization.

Consistent with the above steps, the micron-sized beads select a first population of EVs/exosomes. In the second step, nanometre-sized particles select a specific sub-set of the first population. Merely for example, this sub-set may comprise cancer or other disease-specific exosomes or may comprise a tissue-specific exosome. These may also comprise sub-populations of exosomes with regenerative ability or exosomes containing therapeutic value. The micron-sized particles are preferably magnetic beads, of at least 500 nm up to around 5 μm. The microparticles are functionalised with surface-bound binding agents or antibodies, which are attached via cleavable linkers so that the captured particles can later be released. The binding agents are designed to bind with universal markers present on EVs/exosomes. For example, the microparticles may be functionalised to capture only small EVs (sEVs). The cleavable linkers may be a photo-cleavable linker, a disulfide bridge, DNA or RNA spacers, or DNA-RNA hybrids, and the like (not an exhaustive list).

The nanometre-sized particles are preferably gold nanoparticles (GNPs) of at least 50 nm up to around 300 nm. In some examples, the nanoparticles may be made of materials other than gold. It is generally beneficial for the nanoparticles to be biocompatible, conductive and metallic, however. The nanoparticles are functionalized so that they recognize surface markers only present on a sub-population of EVs.

The antibodies are linked to the microparticles through cleavable linkers so that the captured exosomes can later be released. Preferably, the cleavable linkers used to functionalise the nanoparticles are different cleavable linkers to those used on the microparticles, such that cleaving can be performed in two steps. The nanoparticle's cleavable linkers may nevertheless be photocleavable, disulfide bridges, and DNA or RNA spacers cleavable by enzymes, or DNA-RNA hybrids (the list is not exhaustive).

The nanoparticles may, additionally, be prepared with ssDNA, ssRNA or other molecules which, in some embodiments, might facilitate the simultaneous release of target-specific exosomes with only one cleaving step. This specific example is described by FIG. 3 below. This example can generally be constructed in a way that only EVs/exosomes bound to two particles (i.e. the microparticles and the nanoparticle) are released for downstream characterization/quantification.

Advantageously, the process can be repeated such that cascades of isolations can be effected, using differently functionalised nanoparticles in order to obtain an ultra-refined selection of EVs (such as a highly specific sub-population of exosomes). Therefore, two, three, or even more surface biomarkers present on a target population of particles can be used in sequence in order to obtain a refined sub-population of target particles. Therefore, there is provided an advantageous approach for single discrete EV/exosome characterization from a large population of biomolecules.

The approach can also be used to initially select exosomes from a specific tissue and then, to identify disease-specific exosomes (i.e. exosomes expressing a biomarker indicative of disease) from those tissues. This is relevant because some disease biomarkers, identified in/on exosomes, are expressed in several tissues, yet only expression from some tissues is indicative of disease. For example, in Alzheimer's disease, amyloid Beta deposits in the brain may be used as a marker of the disease. Amyloid Beta also crosses the blood-brain-barrier and can be detected in blood. However, other organs such as the liver also produce amyloid Beta which is also released into the blood. By selecting, in a first instance, brain-specific exosomes such as those carrying NCAM, L1 CAM or GLAST (which are not present in other organs), then a second selection step to identify those brain exosomes that carry amyloid beta we can guarantee that any amyloid β-containing exosome that is captured has originated from the brain, and not the liver. Furthermore, the presence of these brain-derived exosomes that express Aβ can be used to diagnose Alzheimer's disease.

Furthermore, the content of exosomes has been shown to change when organs or cells within an organism transition from healthy to diseased. Therefore, the same exosomes that originate from a particular organ can internally contain disease-markers. It is therefore beneficial to be able to isolate an intact exosome, and subsequently lyse the exosome in order to characterise the internal contents of the exosome.

Isolation Example 1: Photo-Cleavage

FIG. 1 show the steps of a first specific exosome isolation strategy 100, which uses magnetic microparticles 104 as exosome capture particles that are functionalised via photo-cleavable linkage 110 molecules. This example also illustrates the use of Gold nanoparticles (GNPs) 116 as target-exosome capture particles that are functionalised via disulfide linkages 114. The photo-cleavable linkage molecules 110 on the magnetic microparticles 104 are terminated with generic antibodies 108 (i.e. antibodies that are receptive to surface markers (e.g. transmembrane proteins) of exosomes or small extracellular vesicles (sEVs) in general). The disulfide linkages 114 on the GNPs 116 are terminated with a further antibody 112 that is receptive specifically to surface markers on the target exosome 106 (or small extracellular vesicle) of interest.

Beneficially, the disulfide linkages 114 on the GNPs 116 cannot be cleaved under the conditions used to cleave the photo-cleavage linkers 110 on the magnetic particles 104. Thus, two separate cleavage steps are possible.

FIG. 1*a* illustrates an EV capture step, where the generic antibodies 108 on the microparticles 104 bind with all EVs, sEVs, and exosomes, including non-target EVs 102.

In some examples, the generic antibodies 108 specifically bind only to sEVs and/or exosomes or even a specific population or subpopulation of exosomes.

FIG. 1*b* illustrates a target-EV capture step, in which the GNPs 116 bind to the target-EVs 106 only. Thus, non-target EVs 102 or sEVs, which bound to antibody-terminated linkers of the microparticles 104, are not captured by the GNPs 116. Therefore, the result of this step is that the target EVs 106 are bound to exactly two particles: one microparticle 104 and one GNP 116.

Advantageously, the ratio of the size (i.e., a diameter) of the microparticle 104 to the size of the EVs 102, 106 is designed such that bound target EVs 106 are dispersed evenly over the larger surface of the microparticle. Thus, no two EVs are proximate to each other, which has the advantage of ensuring that, in step 1*b*, the GNPs are very unlikely to bind to two target EVs. Preferably, a size dimension (i.e. diameter) of the microparticle 104 is about an order of magnitude greater than the EVs. This beneficial size ratio is described in more detail in FIG. 5.

FIG. 1*c* illustrates a first cleavage step wherein the photo cleavable linkers 110 are dissociated to release all EVs 102, 106 bound to the magnetic microparticle 104. The photo cleavage step may be effected by exposure to UV or near-UV light. The target EV is still bound to the GNP after the photo cleavage step, because the disulfide linkage molecules on the GNP are not photo-cleavable. The magnetic microparticles 104 are subsequently extracted by application of a magnetic field. The non-target EVs 102 and the target EVs 106 (each one bound to a GNP 116) remain in the mixture after extraction of the magnetic particles 104.

FIG. 1*d* illustrates a separation step that separates the unbound non-target EVs from the target EVs 106 that are bound to the GNPs 116. Separation techniques may comprise centrifugation, which extracts the bound target-EV-GNP assemblies due to their greater mass and volume than the unbound EVs. Preferably, the separation is effected by application of an alternating electric field (not shown) which induces a dielectrophoretic force (DEP) acting on the GNP (and to a lesser extent to the EVs) 116. The GNPs 116 thus drag the bound target-EV 106 to a region from where the DEP originates (attraction) or to a region farther from it (repulsion). The DEP technique with the attraction feature is described in more detail below in FIG. 9.

FIG. 1*e* shows a second cleavage step in which the disulphide bond 114 linking the GNP 116 and the target EV 106 is cleaved. The cleavage is effected by treatment with a suitable reducing or alkaline reagent. For example, many suitable thiols can be used, where excess thiol is used in order to shift the equilibrium of the cleavage reaction to the right. Suitable thiols include as β-mercaptoethanol (β-ME) and dithiothreitol (DTT). Alkaline conditions (i.e., higher than pH 8) are also beneficial, in combination with thiols, to effect disulphide cleavage.

The second cleavage step of FIG. 1 causes the target EV 106 to dissociate from the GNP 116. A further centrifugation or DEP step can then be used to separate the unbound GNPs from the unbound target EVs in order to extract the target. The extracted target EV 106 can then be used for further downstream applications such as lysing to characterise the internal and external contents of the EV. Alternatively, the steps of FIGS. 1*a* to 1*e* can be repeated a plurality of isolated target EV 106, to obtain a refined sub-population of the target EVs. Specifically, a second GNP can be used with a further specific antibody that is receptive to a marker present only on sub-population of the extracted target EVs 106. In this way, a further refinement of the target EV population can be provided, in which a sub-population of the initial target EVs is extracted.

Isolation Example 2: Enzyme Cleavage

FIG. 2 shows the steps of a second specific exosome isolation strategy 200, which uses enzyme-cleavable linkages and disulfide linkages. Generally, the receptors 108, 112, the microparticles 104 and the GNPs 116 onto which the receptors are linked, are the same as described in FIG. 1. Generic antibodies 108 (which alternatively are any suitable EV-specific binding agent protein) are attached to the microparticles 104 via RNA or DNA linkers 202. As a further alternative, the generic binding agents 108 may be specific to all exosomes, but not EVs generally, such that only exosomes (and not larger EVs) may become bound to the microparticles. Target-specific binding agents 112 (e.g. antibodies) are attached to the GNPs again via disulphide bonds. Beneficially, the disulfide linkages 113 on the GNPs 116 cannot be cleaved under the conditions used to cleave RNA or DNA linkers 202 on the magnetic beads 104. Thus, two separate cleavage steps are possible.

Figures 2A, 2B, 2C, 2D, 2E:
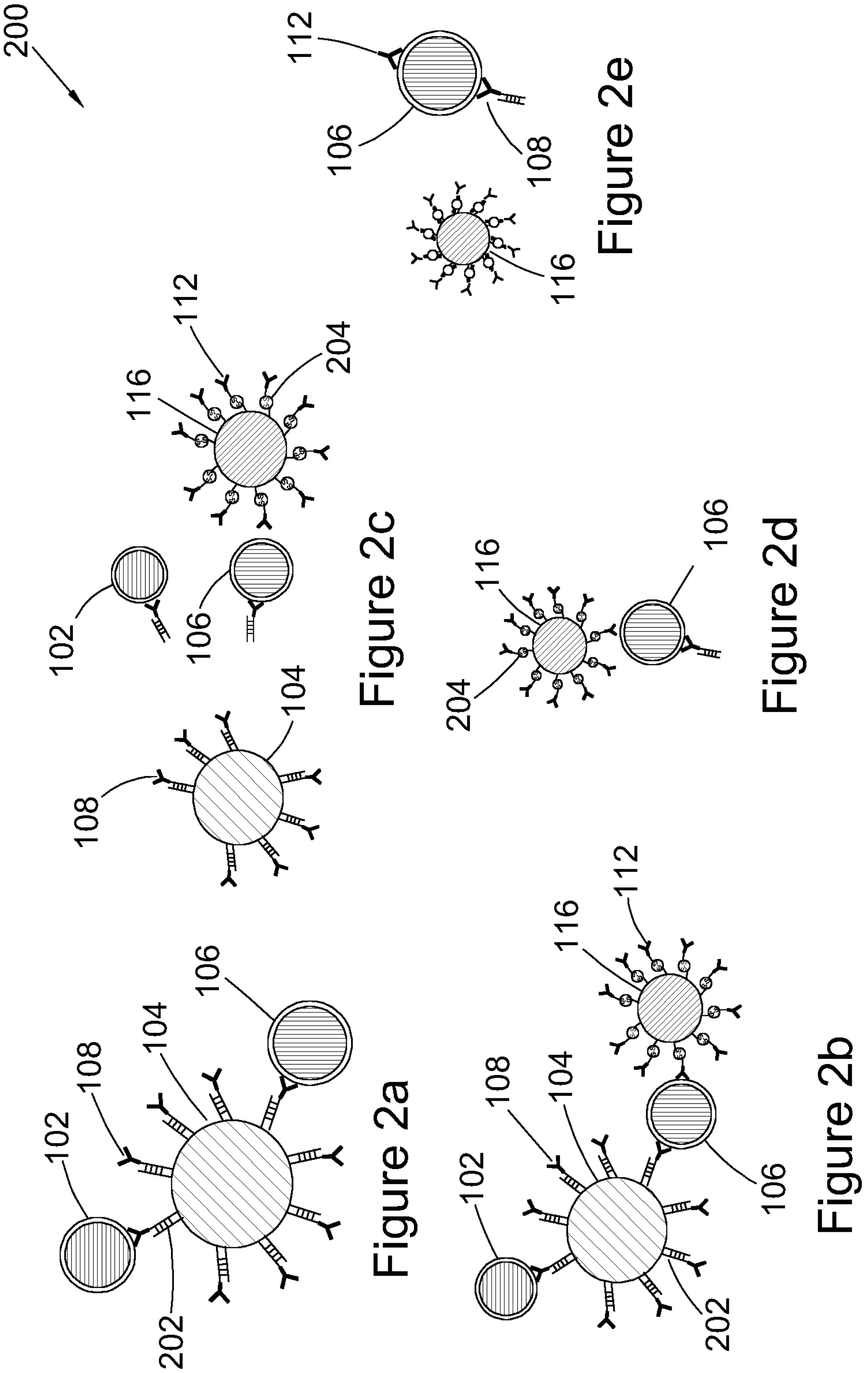
FIGS. 2*a*-2*e* show part of an example exosome isolation strategy using enzyme-cleavable linkages and disulfide linkages.

FIG. 2*a* illustrates an EV capture step, where generic antibodies 108 on the microparticles 104 bind with all EVs, sEVs, and exosomes, including non-target EVs 102 and target EVs 106.

FIG. 2*b* illustrates a target-EV capture step, in which the binding agents 112, e.g. antibodies, of the GNPs 116 bind to the target-EVs 106 only. Non-target EVs 102 are not captured by the GNPs 116. Therefore, the result of this step is that the target EVs 106 are bound to exactly two particles: one microparticle 104 and one GNP 116. Similar to FIG. 1, preferably the microparticles surface area is at least 100 times larger than the EVs 102, 106, such that it is very unlikely that any two target EVs 106 will be bound proximate to one another on the surface of the microparticle.

FIG. 2*c* shows a first cleavage step wherein the enzyme-cleavable linkers are dissociated, resulting in the release all EVs 102, 106 bound to the magnetic microparticle 104. Cleavage is effected by treatment with an enzyme, for example a nuclease, suitable for digesting/cleaving RNA or DNA strands.

FIG. 2*d* illustrates a separation step equivalent to that shown in FIG. 1*d*. Non-target EVs 102 are separated from target EVs 106 that are bound to the GNPs 116. The separation uses any technique that exploits the size or density difference between the unbound non-target EVs and the (larger) target EV-GNP assemblies (e.g., centrifugation). Alternatively, the separation technique may exploit the conductivity of the GNP, e.g. using DEP to isolate the target EVs 106. In detail, the DEP is enabled by the relatively higher polarizability of the GNP relative to the surrounding medium.

FIG. 2*e* shows a second cleavage step equivalent to that shown in FIG. 1*d*, in which the disulphide bond 114 linking the GNP 116 and the target EV 106 is cleaved. Again, the cleavage is effected by treatment with a suitable reducing or alkaline reagent.

Isolation Example 3: Enzyme Induced RNA/DNA Hybrid Cleavage

FIG. 3 shows the steps of a third specific exosome isolation strategy 300, which may be referred to a molecular beacon isolation strategy. Generally, the receptors 108, 112, the microparticles 104 and the GNPs 116 onto which the receptors are linked, are the same as described in FIG. 1.

Generic binding agents 108 (e.g. antibodies specific to all exosomes) are attached to the microparticles 104 via a single strand of RNA or DNA 302*a*. In one embodiment, the length of this single strand nucleic acid would be between 50 bp and 100 bp. The single-stranded linker 302*a* is itself configured to bind with a second corresponding single-stranded RNA/DNA link (i.e. it's complimentary sequence). Target-specific binding agents 112 (e.g. antibodies) are attached to the GNPs again via RNA or DNA linkages 304. In one embodiment, the RNA or DNA linkages are preferably between 50 and 100 bp. In addition, the GNPs 116 further comprise a tendril 306, having a sequence complimentary to the RNA or DNA linkage and forming a double strand duplex with that linkage, the tendril is further terminated with a single strand 302*b* of RNA or DNA. This single RNA/DNA strand 302*b* is configured to extend around a target EV 106 in order to reach its complimentary RNA/DNA strand 302*a* which forms the microparticle linkage. In one embodiment, the tendril 306 is between 200 to 1000 bp, more preferably between 300 and 900 bp and even more preferably between 300 and 700 bp. As such the length of the single strand RNA or DNA strand would be around 200-300 nm in length and would be long enough to bind by proximity to the DNA/RNA probe on the nanoparticle but small enough so that the tendril does not bind to adjacent DNA or RNA molecules. Thus, the single RNA/DNA strand 302*a* on the microparticle is configured to bind with the single-stranded terminus 302*b* of the tendril 306 to form a double-strand of RNA/DNA 302*c*.

Figure 3E:
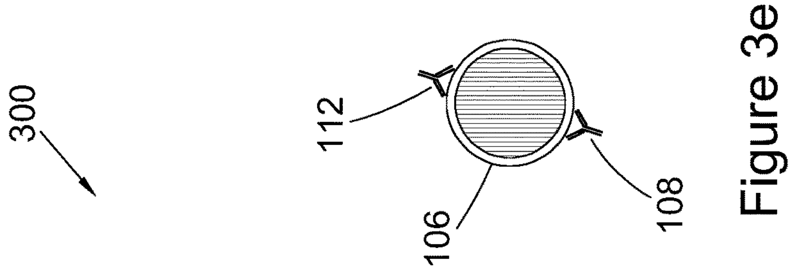
FIGS. 3*a*-3*e* show part of an example exosome isolation strategy using RNA/DNA hybrid molecular beacons.
Figure 3C:
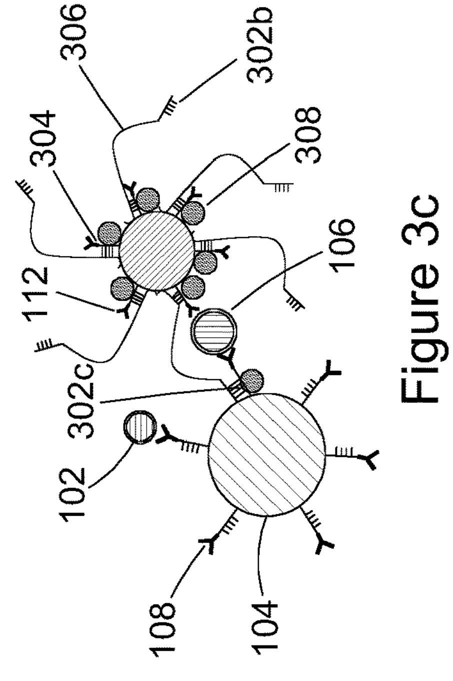
Figure 3D:
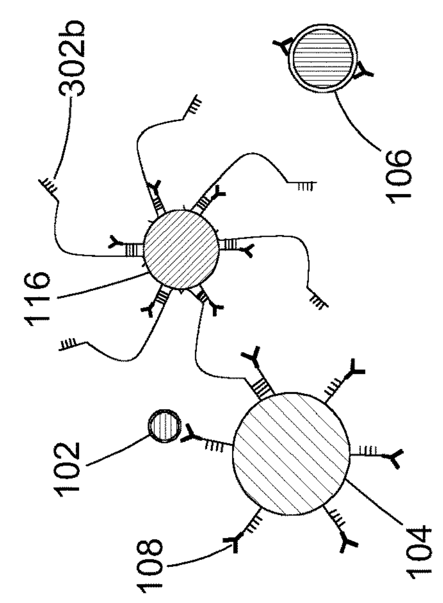
Figure 3A:
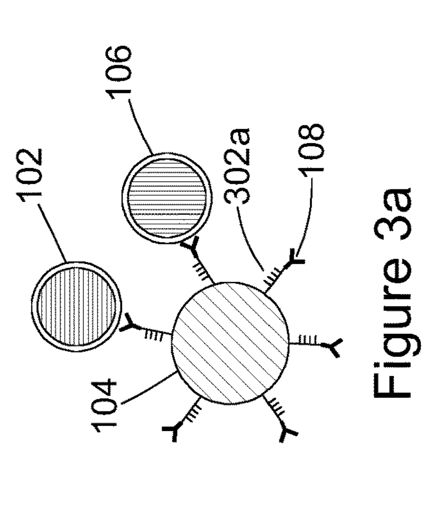

Beneficially, in this isolation strategy, only a single cleavage step is needed to isolate the target EV from the assembly formed of the magnetic microparticle, the target 106 and non-target 102 EVs, and GNPs. This is enabled by virtue of the fact that an enzyme is used to cleave RNA/DNA doubles-strand linkages, but which does not act on single-stranded RNA/DNA links. The method is as follows:

FIG. 3*a* illustrates an EV capture step, where generic antibodies 108 on the microparticles 104 bind with all EVs, sEVs, and exosomes, including non-target EVs 102 and target EVs 106.

Figure 3B:
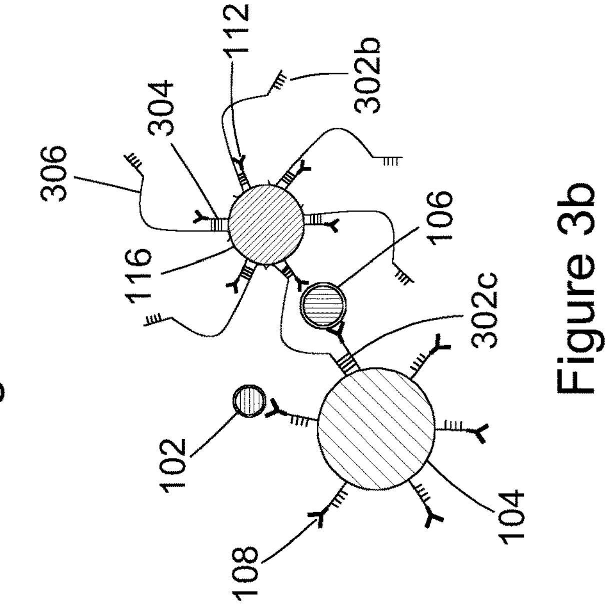

FIG. 3*b* illustrates a target-EV capture step, in which the binding agents 112 of the GNPs 116 bind to the target-EVs 106 only. Additionally, the tendril 306, terminated with a single strand of DNA/RNA 302*b*, extends around the captured target EV 106 to reach the microparticle linkage strand 302*a*. The two single strands 302*a*, 302*b*, then bind to form a doubles-stranded linkage 302*c*.

Non-target EVs 102 are not captured by the GNPs 116. Therefore, the result of this step is that the target EVs 106 are bound to exactly two particles: one microparticle 104 and one GNP 116. Similar to FIGS. 1 and 2, preferably the microparticle are at around two orders of magnitude (at least 100 times) in terms of surface area larger than the EVs 102, 106.

FIG. 3*c* shows the single cleavage step, which uses an enzyme 308 capable of cleaving only double-stranded RNA/DNA linkages. Thus, the RNA/DNA linkage 304 originally comprised of the GNP 116 and the newly-formed DNA/RNA linkage 302*c* are simultaneously cleaved. This has the advantage that the target-EV is released in a single step.

FIG. 3*d* illustrates a separation step. In contrast to FIGS. 1*d* and 2*d*, the target EV 106 is already isolated (and unbound) at this point. Therefore, centrifugation alone is able to separate the target EV from the larger microparticle 104 and GNP 116. Alternatively, or additionally, a magnet may be used to extract the magnetic microparticles 104, and/or DEP may be used to extract the GNPs, in order to obtain a clean solution comprising only the target EV 106.

Furthermore, non-target EVs 102 are still bound (via a single strand of DNA/RNA 302*a*) to the microparticle, and are therefore extracted with the microparticle (by e.g. centrifugation or application of a magnetic field.)

FIG. 3*e* illustrates the formation of a 'clean' solution comprising only the target EVs, after the Microparticles 104 and the GNPs 116 have been removed from the mixture. The EVs can then be assessed in down-stream characterisation or quantified, as described below in more detail.

FIG. 4 show the individual nanoparticles, microparticles, and target biological entities—e.g. EVs present in the isolation strategies described above, and in relation to FIGS. 1-3.

FIG. 4*a* shows the magnetic microparticles 104, otherwise referred to as an EV capture particle, a non-target EV 102, a target EV 106, and a GNP 116. The GNP is otherwise referred to as a target-EV capture particle. The microparticle 104 is functionalised with a ubiquitous binding agent 108, which is receptive generally to a subset of EVs, for example, all exosomes. Thus, larger EVs, proteins, and cell fragments, will not become bound to the microparticles via the generic EV binding agent 108. Preferably, the generic binding agent 108 is an antibody, which is receptive to a surface (transmembrane) protein on the surface of a subset of EVs. Other generic binding agents may include antigen-binding fragments or aptamers.

Where the EVs of interest are exosomes in general, the generic binding agent 108 may be receptive to tetraspanins on the surface of the exosomes.

The general binding agent 108 is attached via a photo-cleavable linker 110 in FIG. 4*a*, in accordance with the isolation strategy described in FIG. 1. This photo-cleavable linker can generally be dissociated by exposure to UV or near-UV light.

Figure 6:
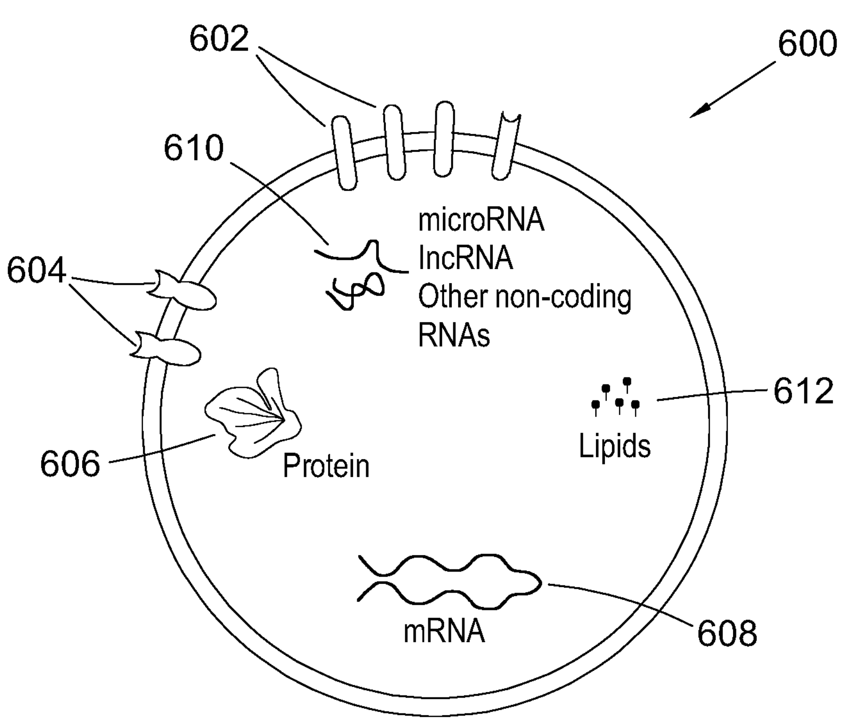
FIG. 6 illustrates the general structure of an exosome.

The GNP is functionalised with a specific binding agent 112, which is receptive to a (target) subset EVs 106 within the larger set of generic EVs 102 captured by the microparticle 104. Again, preferably the specific binding agent 112 on the GNP 116 is an antibody that is receptive to an antigen/protein on the surface of the target EV 116. For example, the target EV may be an exosome that is indicative of a particular disease or cancer, where the specific binding agent 112 is receptive to a disease biomarker. For example, the HER2 protein can be targeted as a disease biomarker, which is present on exosomes associated with breast cancer. For example, the HER2 protein may be marker 604 as shown in FIG. 6. In this example, the specific binding agent 112 on the GNP 116 is a HER2-binding agent, such as Herceptin (Trastuzumab) or a HER2-binding fragment thereof. The specific binding agents 112 are attached to the GNPs 116 via disulfide bonds 114 that cannot be cleaved by UV light. The disulphide linkers 114 are cleaved in alkaline conditions with a suitable reducing agent, such as a thiol.

FIG. 4*b* shows a further microparticle 104 and GNP 116, respectively functionalised with generic 108 and specific 112 binding agents. This figure illustrates that generally the binding agents can be functionalised with any suitable linker 402, 404. Preferably, the linkers 402, 404 on the microparticle and the GNP, respectively, are different such that two separate cleavage steps can be effected. This is advantageous because it allows the microparticle to be cleaved from the target EVs 106 and extracted (e.g. by application of a magnetic field), before the GNPs 116 are cleaved in a second step from the target particles 106. After the second cleaving step, the GNPs 116 are extracted via centrifugation, or DEP, in order to isolate the target EVs 106.

FIG. 4*c* shows the microparticle 104 and GNP 116 consistent with the method used in FIG. 3, i.e. the molecular beacon method. The single strand of RNA/DNA 302*b* which terminates the tendrils 306 of the GNP 116, are configured to bind with the single strand RNA/DNA linkages 302*a* on the microparticle. Thus, the linkages 302*a* of the microparticle cannot be cleaved by an RNA/DNA cleaving enzyme 308 until a double strand (not shown in FIG. 4) of DNA/RNA is formed.

Figures 5A, 5B:
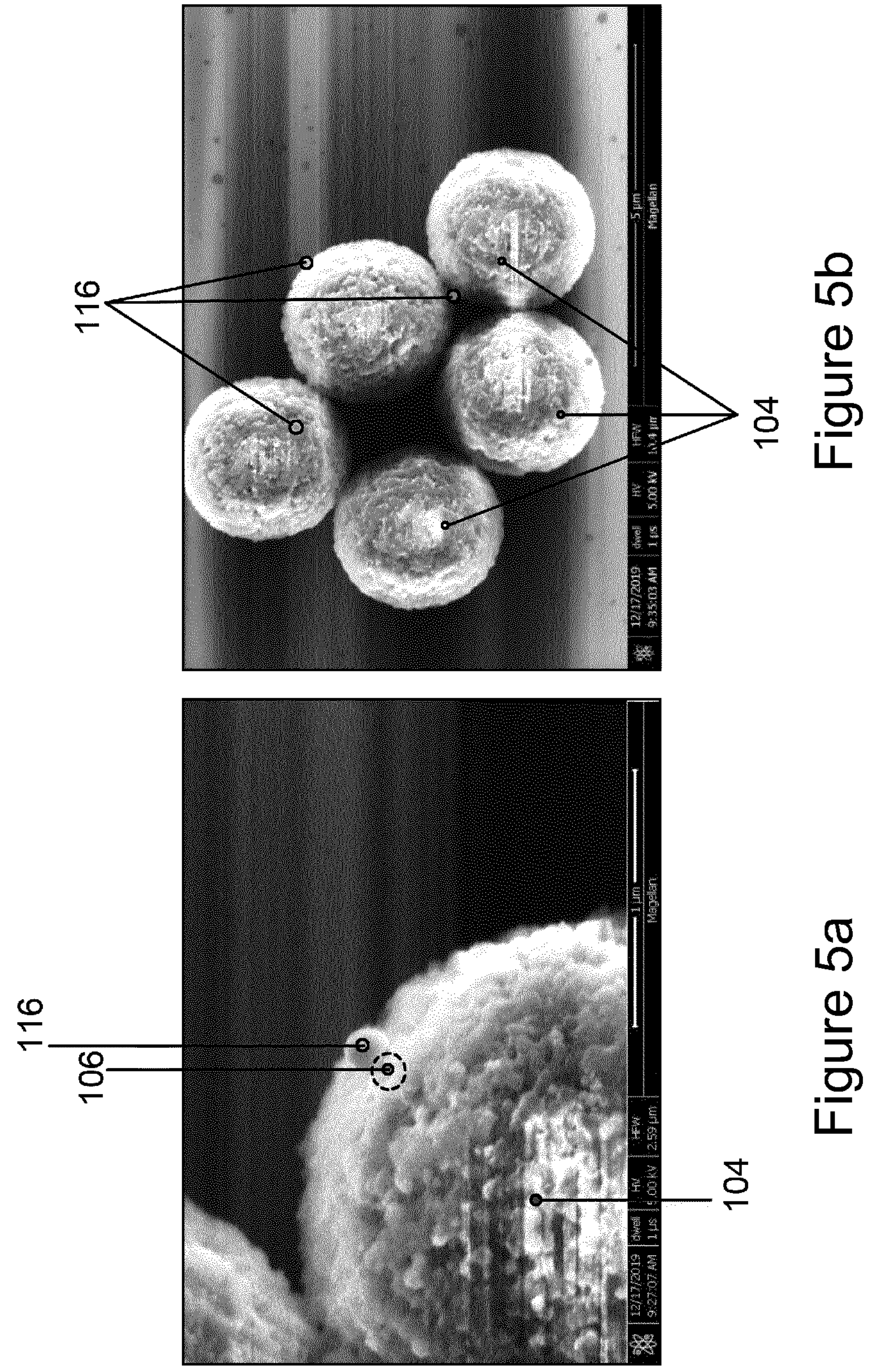
FIGS. 5*a* and 5*b* each show scanning electron microscope images of magnetic beads with highlights showing positions of bound target exosomes and nanoparticles.

FIGS. 5*a* and 5*b* show scanning electron microscope images of magnetic beads 104 with highlights showing positions of bound target vesicles 106, captured by GNPs 116. In general, the magnetic microbeads 104 function as EV capture particles, and the GNPs function as target-EV capture particles 116, which capture only a subset of the particles captured by the microparticle 104.

In general the size ranges of the particles may be as follows:

- Target EVs 106 and EVs in general 102: 40-160 nm
- Magnetic microparticles: >1 μm e.g. 2-3 μm in diameter, when spherical (which is not necessarily the case), or in average minimum dimension
- GNP/target-EV capture particles: 50 to 300 nm in diameter, when spherical.

The relative size of the microparticle 104 to the GNP 116 can be seen in FIG. 5. As mentioned above, the surface area ratio of microparticle 104:GNP 116 is at least 100, but can be up to around a 1000 times greater. Consistent with the above size ranges, in one example, the GNP is 200 nm in diameter and 0.13 $\mu m^2$ in surface area, and the microparticle is 2.7 μm in diameter and 22.9 $\mu m^2$ in surface area, such that the surface area ratio between the GNP and the microparticle is 182.

It not necessary for the particles to be spherical as shown. However, it is advantageous for the size (dimension) of the microparticle to be sufficiently large that the microparticle 104 has a substantially larger surface area that that of the GNP 116. A large surface area on the microparticle creates a large amount of available binding space for EVs. Thus, even at high concentration of EVs, it is unlikely that two EVs will bind proximate to each other on the surface of the microparticle. In more detail, no two EVs will bind on the microparticle surface at a separation of less than 300 nm, or, the size dimension of the GNP. Thus it is very unlikely that two EVs (generic 102 or target 106) will bind onto the surface of the microparticle 104 such that a GNP is able to bind to both EVs.

It is therefore beneficial to keep the size of the GNP relatively small (e.g. at least 10 times smaller in length) compared to the microparticle, to reduce the likelihood that a GNP is able to bind to two EVs at once. By maintaining the above ratio between microparticle and GNP size, it becomes unlikely that a GNP will bind to two EVs.

After an isolation method has isolated a target EV in accordance with either FIG. 1*d* or FIG. 2*d*, it will therefore be appreciated that each target EV 106 is bound to exactly one GNP 116. This is beneficial for quantification sensing purposes, as it is possible to detect the number of EVs captured by measuring a current. The GNPs, bound to the EVs, enable an electrical current to be detected. This quantification sensing is derived in detail below, corresponding to FIGS. 7-9.

FIG. 6 illustrates the general structure of an exosome 600, including general markers 602 and more specialised/specific (e.g., disease or tissue-specific) markers 604. Generally speaking, exosomes provide indicators for a variety of biological responses in humans and other organisms. Exosomes are associated with various diseases including cancer, and diseases involving the cardiovascular and nervous systems. Exosomes are understood to provide a variety of functions within humans, for example: removal of cell constituents, and potentially as a mechanism to communicate between cells as part of a regulatory system.

Exosomes comprise a cell membrane made of a lipid bilayer, as shown, and are therefore a subset of extracellular vesicles (EVs). Exosomes are generated by cells and therefore contain, within the boundary of the lipid bilayer, a variety of cell constituents including e.g.: nucleic acids, proteins 606, lipids 612, RNA and DNA fragments, and various subcategories of RNA and DNA 610 (e.g., mRNA 608, microRNA, Y-RNA, mtRNA, mtDNA, dsDNA, ssDNA, and the like).

Furthermore, the surface of exosomes carries various hallmarks 602 that are exosome-specific, and therefore allow exosomes to be differentiated from other EVs, and cell fragments. These hallmarks 602 include tetraspanins, other GPI-anchored (Glycosylphosphatidylinositol anchored) proteins, integrins, and proteins with lipid or membrane protein-binding ability. Furthermore, other cytosolic or periplasmic proteins with lipid/membrane-binding ability may also be targeted, for example, ESCRT-I/II/II (such as TSG101 or CHMP), or accessory proteins such as ALIX.

Tetraspanins found on the surface of exosomes in general includes: CD9, CD63, CD81, CD326, CD82, CD37 and CD41. Tetraspanins demonstrate the presence of a lipid bilayer. Other surface-anchored proteins that are typically universal to exosomes includes the following, which is not an exhaustive list (MHC class I (HLA-A/B/C, H2-K/D/Q), integrins (ITGA/ITGB), transferrin receptor (TFR2), and Heparan sulfate proteoglycans.

The ability to isolate exosomes based on these hallmarks 602 avoids the accidental isolation of contaminants such as lipoproteins, protein aggregates and exomers. In other words, the ability to reliably capture and isolate exosomes on the basis of exosome-specific surface proteins significantly reduces the probability of a false positive.

Referring back to FIGS. 1*a*, 2*a*, and 3*a*, a general population of EVs including target and non-target EVs 102, 106 is typically sequestered based on binding with any one of the above mentioned universal/hallmark surface markers 602. Subsequently, corresponding to FIGS. 1*b*, 2*b*, and 3*b*, the target-capture particles (i.e., the GNP 116) bind to a specific membrane biomarker that is present only on a subset of the initially captured EV. Examples of specific biomarkers 604 include proteins expressed by certain diseased cells, including GPC1 for various cancers, and HER2 for specifically breast cancer.

It will therefore be understood that a subpopulation of EVs or exosomes can be isolated based on specific biomarkers 604, which may be disease-specific biomarkers. Therefore, beneficially, the mere detection of the presence of this subpopulation of EVs or exosomes 600 can suggest a disease.

Another advantage is that the isolation and detection maintains the integrity of the exosome, and its contents (606, 608, 610, 612) are not lost. Therefore, an isolated population of exosomes can be lysed to characterise the complete content of the exosome, including the internal contents (i.e., proteins 606, mRNA 608, non-coding RNAs 610, and lipids 612). Thus, in addition to the isolation process which itself can indicate certain diseases, further characterisation of the internal contents can be used to provide confirmation of said particular disease, or provide a first indication of a disease/condition. In this regard, the following disease-specific biomarkers are known to be cytosolic (i.e. internal) and may be used to indicate or confirm a disease: Microtubule-associated Tau; Heat shock protein HSP70, and various other DNA, RNA, lipids and proteins.

Apparatus for Extracting and Sensing GNP Particles Bound to EVs

Figure 7:
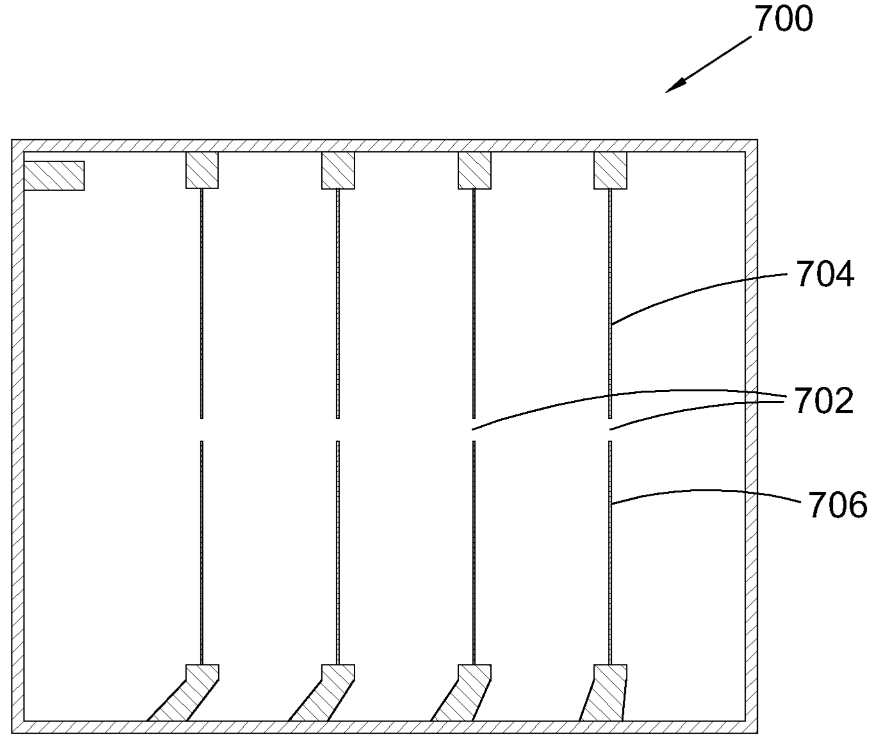
FIG. 7 illustrates an apparatus suitable for extracting nanoparticles bound to target molecules using dielectrophoresis.

FIG. 7 shows an array of five electrode pairs with a nano-gap, i.e. a separation between the tips of the electrodes of around 100 nm, or preferably less.

Each of the nano-gaps 702 defines a sensing regions, or a DEP focusing region, dependent on the mode of operation of the device. Each of the electrodes 704, 706 of each electrode pair are typically gold, and are fabricated such that the tips of the electrodes approach each other in order to produce a nano-gap of less than around 100 nm. An array of sensors 700 as shown here may comprise far more than 5 electrode pairs. For example, more than 10 or 100 sensors 700 may be used, each comprising a plurality of sensing/DEP regions 702.

In use, for example to attract and characterise the presence of GNP-exosome assemblies, an alternating current can be applied to the sensor 700, which in turn induces an alternating electric field emanating from the sensing regions 702. The electric field may be used to attract GNPs and concentrate them around the sensing region 702. Each sensing region 702 may then be used to apply a direct current to characterise a response of each of the regions, to identify and quantify the presence of GNPs.

Figures 8, 9:
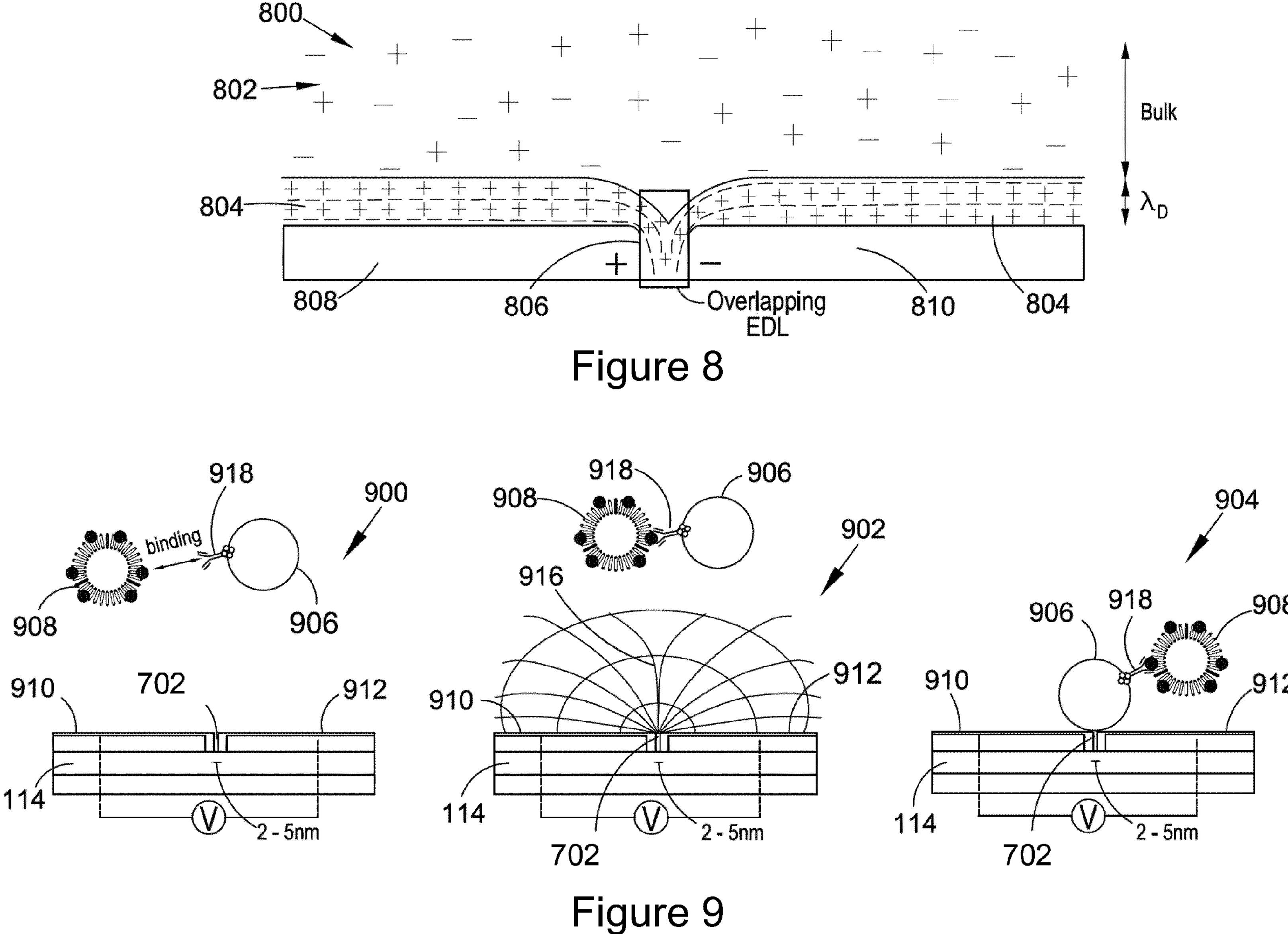
FIG. 8 illustrates a profile cross-sectional view of an electrode pair with a nano-gap, and an electrical double layer in the surrounding fluid.
FIG. 9 illustrates a method of using dielectrophoresis (DEP) and current measurements to capture and detect a target particle using metal nanoparticles.

FIG. 8 illustrates a sectional view of an electrode pair with a nano-gap in a model liquid containing charged entities. An electrical double layer is present in fluid immediately adjacent to the electrodes 808, 810. In this sensor example 800, individual ions 802 persist in the medium, and concentrate over the electrodes' 808, 810 surface to form the double-layer 804. This double layer can be seen to overlap in the sensing region between the electrodes 806.

Advantageously, the separation between the electrodes 808, 810 is small enough such that the electrical double layer (EDL) present over each electrode 808, 810 overlaps in the sensing region. That is, the EDL overlaps in the nanogap 806. This overlap is beneficial for capturing of targets (i.e. gold or other conductive nanoparticles), and the subsequent sensing/quantification of said target particle. Thus it can be useful for the lateral distance between the pair of electrodes to be less than twice the width of the EDL in the surrounding solution. In some implementations, the lateral distance between the pair of electrodes may be sufficiently small to ensure this.

Generally, an EDL is a structure that appears on the surface of a charged surface object when it is exposed to a solution with dissolved ions. The double layer refers to two parallel layers of charge surrounding the surface (e.g., the electrode surface). The first layer comprises ions adsorbed onto the surface due to either chemical interactions and/or a charged electrode surface. The second layer is composed of ions attracted to the first layer via the Coulomb force, where the ions electrically screen the first layer. In this way, the width of the EDL may be seen as equivalent to the Debye length in an ionic solution. The Debye length is generally a property of an ionic solution, and is a measure of a charge carrier's net electrostatic effect, and to what extent said effect persists in the solution. Every Debye-length $\lambda_D$ [m], the electric potential will decrease (i.e. be screened) in magnitude by 1/e. The width of electrical double/Debye layer is a function of at least the ionic strength of the fluid. Moreover, the Debye length may be on the order of a few nanometres on an electrode having an applied potential. In implementations, a gap 102 between the electrode pair may need to be less than ~20 nm in order for the Debye length (i.e. EDL width) to be equal or less than half the lateral distance between the pair of electrodes. In some implementations, even narrower gaps 102 may be created, e.g. as low as 5 nm or even 2 nm gaps.

The Debye length is related to ionic strength of the fluid, according to:

$$\lambda_D[m] = \sqrt{\frac{\varepsilon_0 \varepsilon_T k_B T}{\sum (z_i q)^2 c_i}}$$

where z represents ionic species, and q their corresponding charge values.

Alternating electric fields may be used to induce an electrophoretic force on conductive nanoparticles bound to targets EVs/particles. Thus, conductive nanoparticles such as GNPs may be actively transported to, and concentrated around, a sensing region 702, 806 or nanogap of an electrode pair.

In detail, the time averaged DEP force of a spherical particle with radius R and in a solution with a dielectric permittivity of $\varepsilon_m$ is provided below:

$$F_{DEP}(\omega)=\pi\varepsilon_m R^3 Re(f_{CM}(\omega))\nabla|E|^2$$

The 'real' part of the above Clausius-Mossotti factor (CMF), $Re(f_{CM}(\omega))$, determines the direction of the DEP force based on the dielectric permittivity and conductivity (inside the CMF term) of the solution and particle. With conductive nanoparticles, this force is generally attractive between the nanoparticles and the source of the electric field. The gradient of the E-field in solution squared, $\nabla|E|^2$, correlates with the supply voltage applied across the DEP electrodes. The DEP electrodes may also be the same electrodes 910, 912 as used to characterise and measure the sensing region to detect the presence of the target entity. Additionally, the magnitude and the sign (i.e. attractive or repulsive) of the DEP is also a function of permittivity of a particle (not only conductivity), especially for biological targets. Furthermore, the DEP force can be a function of the frequency of the applied E-field, especially for biological targets. However, for metallic particles, DEP force is generally invariant with respect to the frequency of the applied E-field.

Advantageously, dielectrophoresis (DEP) offers rapid concentration and isolation of nanoparticulate matter that does not depend on specific chemical binding or alterations. The DEP process commonly utilizes two electrodes in solution that are subjected to an alternating electric field (E-field). The force on the particles derives from the fact that the alternating electric field induces local dipoles within the particles. These local dipoles cause a net force toward, or away from, the E-field gradient depending on: the frequency of oscillation, and the relative dielectric permittivity of the particle and surrounding medium.

Detecting Extracellular Vesicles (EVs), by known techniques can require purification by ultracentrifugation or precipitation, and detection through Nanoparticle Tracking Analysis (NTA) or Dynamic Light Scattering (DLS). Both these measure the Brownian motion of nanoparticles, whose speed of motion, or diffusion constant, is related to particle size through the Stokes-Einstein equation. Therefore, such devices are not sensitive to small concentrations of extracellular vesicles such as exosomes and provide almost no information relating to proteins or other biomarkers decorating the surface of EVs.

There is now described a more sensitive system and method, which can produce a high signal-to-noise ratio not only in detecting e.g. exosomes but also in transporting relevant biomarkers.

FIG. 9 illustrates an example of a method of using dielectrophoresis (DEP) to influence and accelerate the transport of nanoparticle-entity assemblies/pairs. FIG. 9 further illustrates the capture and characterization of the target entity 908 with the aid of gold nanoparticles 906. The electrodes 910, 912 are gold in the illustrated example, with a nano-gap of approximately 40-50 nm, although this may be as low as 10 nm or even 5 nm. The electrodes are provided on a substrate 114.

Target entities 908, such as exosomes, forming part of a biofluid may be sequestered by functionalised nanoparticles 906 as described above. In the example of FIG. 9, the nanoparticles 906 are gold nanoparticles (GNPs). In accordance with the isolation methods described above in relation to FIGS. 1-3, the assemblies comprised an EV 908 and a GNP 906 will preferably comprise no more than two particles.

Step 900 shows a binding/sequestering event taking place in order to form a nanoparticle-target assembly. The microparticle 104 and the steps used to extract and isolate the target particle 106, 908 are not shown illustrated for simplicity.

Step 902 depicts an electric field 916 being applied to the medium such that a force is exerted on the nanoparticle(s) 906. For a DEP force to be exerted on the nanoparticles 906, a relative difference should exist between the conductivity of the nanoparticles and the surrounding medium as described above. Thus, in implementations, GNPs are beneficial because they are more conductive than the dilute medium in which they are suspended. The DEP force draws the GNP 906 and the target 908 towards the sensing region 702. An alternating current should be applied to induce an alternating electric field. In some implementations a frequency of up to about 1.5 MHz may be used.

Step 904 shows the electrophoretic/DEP causing the nanoparticles 908 to be concentrated around the sensing region. Advantageously, the electrodes 910, 912 do not need to be functionalised with antibodies or any binding agent, because GNPs have a natural affinity, i.e. a thermodynamically favourable interaction, with gold electrodes. Therefore, when the nanoparticles 908 become concentrated around the medium due to DEP, the GNPs become effective bound to the region 702 in between the electrodes.

An increasingly narrow lateral separation of electrodes may increase the dielectrophoretic (DEP) force without the need to increase a voltage to power the applied electric field. However, with DEP there can be adverse effects on the sample solution and its analytes due to large trapping voltages. In order to overcome the thermal motion of particles with dimensions under 100 nm, conventional DEP electrodes with micrometre-scale gaps typically require an unfavourable high trapping voltage, for example, a minimum of 10 V. Such large trapping voltages can cause Joule heating, bubble formation, and unfavourable electrochemical reactions.

Implementations of the described system/method have small gaps between the electrodes, e.g. less than ~10 nm, to facilitate bridging this gap with one or a few nanoparticles. This can provide an additional advantage of increasing the DEP trapping force without the need to raise the trapping voltage, mitigating these unfavourable effects. Further, by reducing the width between DEP electrodes, the gradient of the E-field can be increased substantially, which provides a greater force on the GNPs and thus an improved ability to efficiently concentrate the GNPs/nanoparticle-entity assemblies around the sensing region. Ultimately, this can result in a method more sensitive to the presence of target entities, since the nanoparticle-entity assemblies may be collected more efficiently.

An AC voltage may then be applied to the electrodes 910, 912 that induces an alternating E-field in the fluid suspension containing the nanoparticle-entity assemblies in step 902.

After the attraction 902 and concentrating 904 of the nanoparticle-entity assemblies around the sensing region 702, the assemblies bridge the electrode nanogap 102. A direct current is generally then applied, which is used to characterise/measure a response of the sensing region in order to identify whether the assemblies (and thus exosomes) are present. A voltage of around 1 V may be applied to produce a direct current. A baseline current (where no bridging occurs) may be around 1-20 pA. A current produce from a bridged gap (i.e. as seen in step 904) may be around 1-100 nA. Thus, a signal to noise ratio of over a thousand may be achieved in implementations of the described method. Furthermore, when bridging occurs, an activation voltage can be applied which fuses the bridging particles, thus decreasing their resistance; in such examples, currents of 1 mA and above can be carried by the fused bridging nanoparticles.

An Ohmic response (i.e. indicative of classical resistor behaviour) generally indicates that the nanogap sensing region 702 is bridged by GNPs. Therefore, a characteristic linear relationship may be seen when a direct current is applied across the electrodes. However, in other implementations, an AC current may be used to characterise a response of the sensing region. In implementations, the same AC current as used to induce a DEP force in the nanoparticles may be used to characterise an impedance response. In this way, an Ohmic response may still be identified for example, by identifying a characteristic impedance profile of a classical resistor. As a further example, when very narrow electrode gaps are fabricated on the order of 5 nm, non-classical electron transport effects may be seen upon application of a constant voltage to an electrode pair bridged with nanoparticles. Thus, if effects such as tunnelling and flickering resonance are to be expected, the identification of nanoparticle-entity assemblies may comprise identifying a current-response profile different to a classical resistor.

Figure 10:
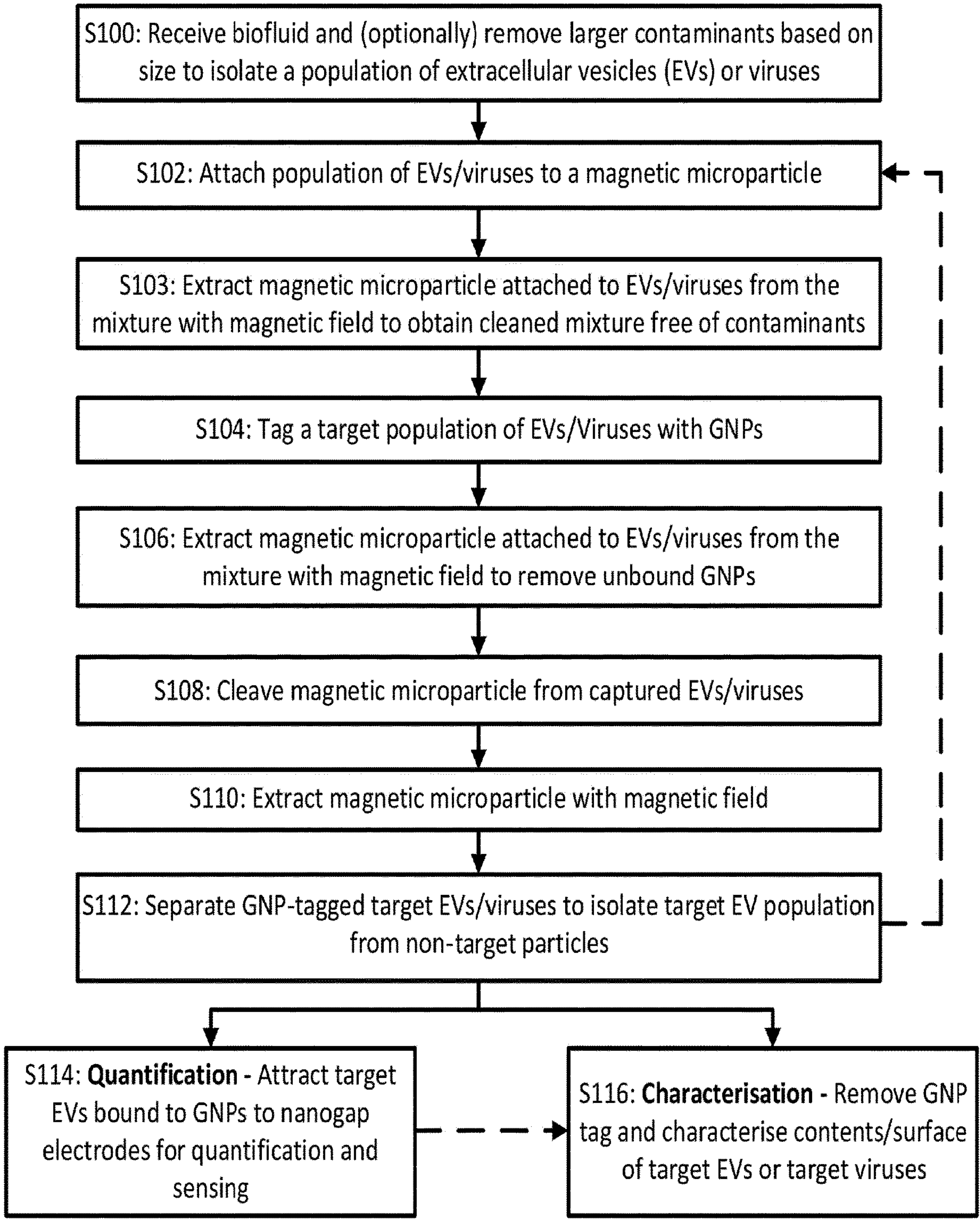
FIG. 10 shows a workflow for the process of isolating a target population of particles from a biofluid.

FIG. 10 shows a flowchart which describes the process of isolating a target population of biological vesicles from a biofluid. It will be understood that the target population can be any of a particular family of EVs or a population of exosomes deriving from a particular organ (e.g. liver) or indicative of diseased cells. The biofluid may initially include EVs of varying sizes, a plurality of different exosome populations, viruses, and the like. The biofluid may further comprise a number of contaminants including: open cell fragments, lipoproteins such as low-density and high-density lipoproteins (LDLs, HDLs), cholesterol, protein aggregates, Ectosomes. This list is not exhaustive.

Step S100 can optionally comprise an initial filtration or isolation step in which large biological particles and contaminates are removed. Thus, suitable separation techniques exploit the relative size of particles, and include: centrifugation, and linear-flow within a microfluidic device that exploits different hydrodynamic radius of particles. Large EVs, large proteins or aggregations can thus be separated from a population of EVs within which the target population is contained.

Step S102 comprises sequestering or capturing a population of EVs, e.g., capturing exosomes or small EVs of a certain size, using micro-sized capture particles that may be magnetic microparticles. Such microparticles 104 are described in detail in relation to FIGS. 1-3.

In Step S103, a cleaning step is performed (using a magnetic field), where the magnetic microparticles are extracted from the mixture in order to separate them from contaminants (including unbound cell fragments, unbound antibodies, and unbound targets). Thus, a cleaned mixture may be obtained prior to S104, where GNPs are introduced.

In step S104, functionalised GNPs are introduced to the mixture, where the GNPs bind to a specific subset of EVs. This step corresponds to FIGS. 1*b*, 2*b*, and 3*b* described above.

In step S106, the microparticles are again extracted from the mixture, carrying with them the captured EVs and target EVs, in order to remove further unwanted contaminants, which in this case include unbound GNPs. This extraction is preferably carried out by application of a magnetic field. However, due to the relative size of the assemblies formed by the microparticles bound to EVs, centrifugation may also be used, which discriminates based on particle size.

As mentioned above, two 'cleaning' steps are performed, both involving application of a magnetic field to sequester the magnetic microparticles and the particles to which they are bound. Sequestering the microparticles thus allows other contaminants in the mixture to be cleaned/washed. For example, in S106, unbound GNPs (the GNPs having been introduced in S104) may be washed away during the extraction of the magnetic micro particles.

The flowchart in FIG. 10 shows two cleaning steps (S103 and S106, which remove contaminants and unbound GNPs, reactively), which is the preferable example of carrying out the isolation method. Alternatively, the GNPs may be added to the mixture to tag the target particles prior to Step S103. In this alternate example, only one cleaning step would be required (i.e., in S103) which would simultaneously remove contaminants and unbound GNPs, and may obviate the need to carry out S106. Irrespective of this, however, the result of the cleaning steps is that a cleaned solution is formed by step S103 which preferably is free from contaminants such as open-cell fragments and larger EVs, as detailed above.

In step S108, the mixture is treated to cleave the magnetic beads away from the particles (EVs) which were sequestered in step S102. Preferably, cleavage is effected by application of UV or near-UV light, which dissociates photo-cleavable linker molecules used to functionalise the microparticles.

In step S110, the microparticles are extracted or separated from the mixture by application of a magnetic field. Following this step, there remains a mixture comprising the target particles tagged with GNPs, and un-tagged non-target particles. This corresponds to FIG. 1*d* and FIG. 2*d*

In step S112, the GNP-tagged target particles are separated from the non-target particles. This may be effected by application of an alternating electric field to induce a dielectrophoretic force (DEP) on the tagged-particles only. DEP is described in detail above in relation to FIGS. 7-9.

After step S112, two alternative applications can follow:

In step S114, the assembly of the tagged target particles is maintained such that the presence of the GNPs can be exploited. Specifically, the GNPs are drawn towards an array of electrodes, for examples as shown in FIG. 7, where an electrical response to an applied current is sensitive to the number of GNPs in the sensing regions 702 of the electrodes. This method of sensing and characterisation using electrodes and DEP is described in detail in related published PCT application, publication number WO 2019/211622 A1.

The target particles are bound to the GNPs in a 1:1 ratio (by virtue of the relative sizes of the microparticles to the GNPs, as described above in relation to FIG. 5) therefore, the number of target particles can be quantified accurately. Beneficially, the target particles can be used subsequently in S116 after S114 because the integrity of the target particles is maintained.

Step 116 involves the characterisation of the target particles. The GNP is cleaved from the target, and extracted via either DEP or centrifugation, for example. The method of cleavage depends on the nature of the linkage used on the GNP; for example, a disulfide linker can be cleaved as described above using suitable reducing agent in alkaline conditions. The surface proteins of the target particles may be characterised without destroying the vesicles, for example, by ELISA (enzyme-linked immunosorbent assay) or other suitable characterisation technique. Furthermore, or alternatively, the target particles can be lysed (e.g., using a simple detergent) in order to free the contents of the vesicles, e.g., cytosolic proteins and RNA etc. The contents can then be characterised using suitable techniques including: ELISA, PCR and RNA/DNA sequencing, mass spectrometry (i.e. for protein characterisation. No doubt many other techniques for characterisation of biomolecules in general will be apparent to the skilled person.

Advantageously, because the steps of the method S102 to S112 maintain the integrity of the target particles, the steps may be repeated as indicated in order to produce a further-refined population of particles. Merely for example, a first pass of steps S102 to S112 may isolate exosomes, from a biofluid mixture containing many non-target exosome families and EVs, which are derived from brain tissue. The brain tissue exosomes isolated by S112 may then be re-introduced in step S102 (after removing the tagging GNP). The steps S102 to S112 are then repeated to isolate a subpopulation of brain-tissue exosomes that contain amyloid-beta deposits.

This is particularly beneficial because other organs, e.g., the liver also, produce amyloid beta. Thus, if amyloid beta-containing exosomes were targeted in the first instance, a non-specific population of exosomes may be captured which derive from multiple different organs (i.e. liver and brain). By selecting in a first instance brain-specific exosomes (which are not present in other organs), and subsequently targeting amyloid beta-containing exosomes, an improved level of specificity is achieved in which a refined sub-population of exosomes can be obtained. Amyloid beta can cross the blood-brain barrier and can be indicative of Alzheimer's disease. Recycling isolated target particles from S112 to S102 is therefore beneficial in diagnosing diseases or conditions that are otherwise difficult to diagnose.

Figure 11:
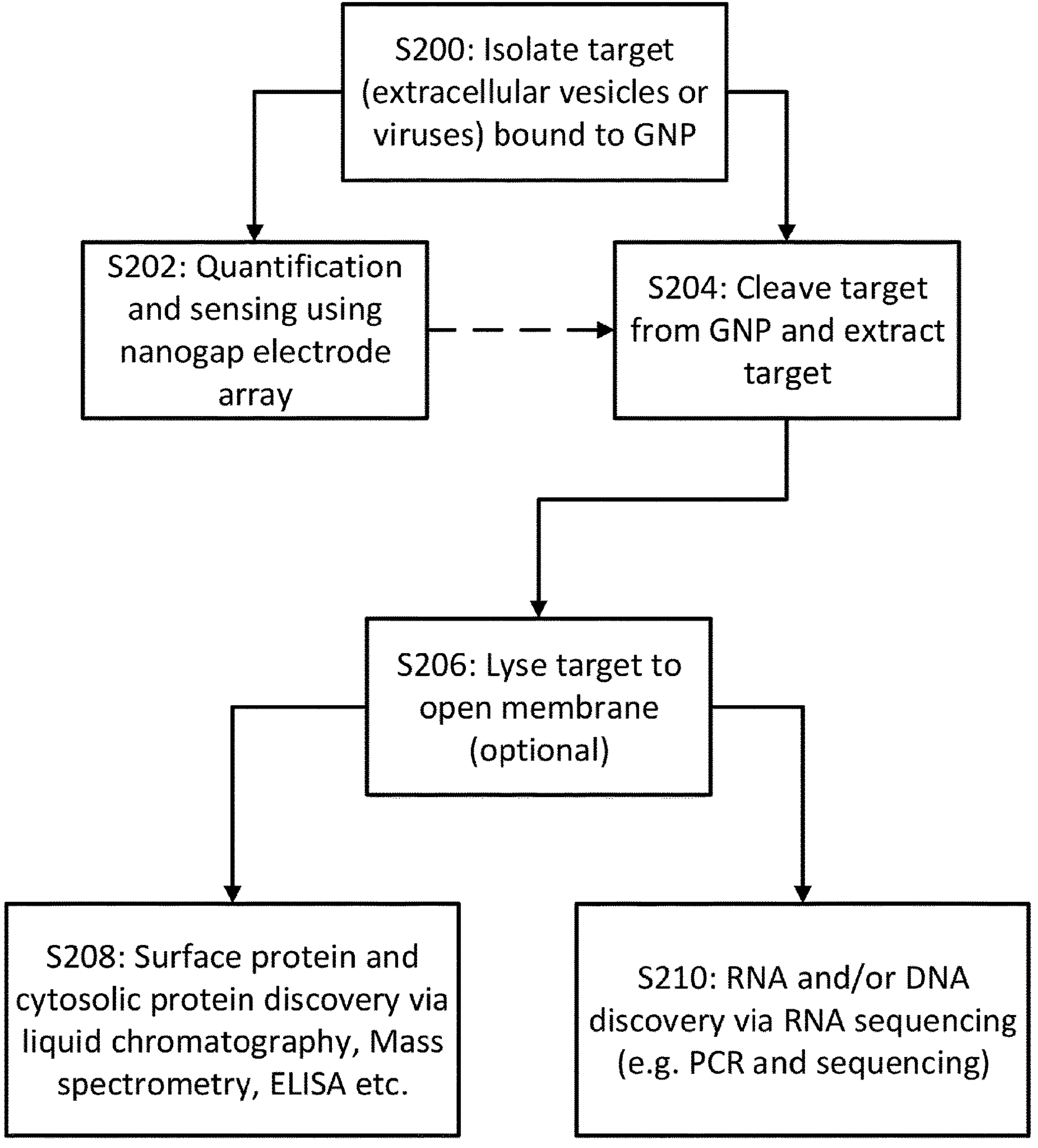
FIG. 11 shows a general workflow for methods of detecting and/or characterising isolated targets.

FIG. 11 shows a more detailed workflow for steps S114 and S116. In step S200, isolated targets are obtained still bound to the GNPs. As mentioned above, target particles can either be quantified in S202 using the electrode array described in FIGS. 7-9, or the targets can be cleaved from the GNPs in step S204. S202 can optionally be followed by cleavage from the GNP and the rest of the steps followed. In step S206, the target particles are lysed (i.e., the cell membranes are destroyed) such that the internal contents can be characterised together with the surface proteins/markers. Nevertheless, it should be appreciated that S206 is optional, and that lysing is not necessary in order to perform the characterisation steps in S208.

Steps S208 and S210 can both be performed, and are not mutually exclusive to one another. Larger proteins are characterised in S208 using techniques such as mass spectrometry or gas chromatography. In step S210, RNA and DNA comprised within the target particles can be identified using sequencing techniques, optionally with suitable amplification techniques such as PCR. Thus, steps S208 and S210 can be used for novel or previously unknown biomarkers or proteins within target populations of EVs. The discovery of novel biomarkers on, for example, exosomes can allow a new sub-population of exosomes to be targeted (i.e., with GNPs functionalised with suitably specific antibodies) based on the novel markers.

Figure 12:
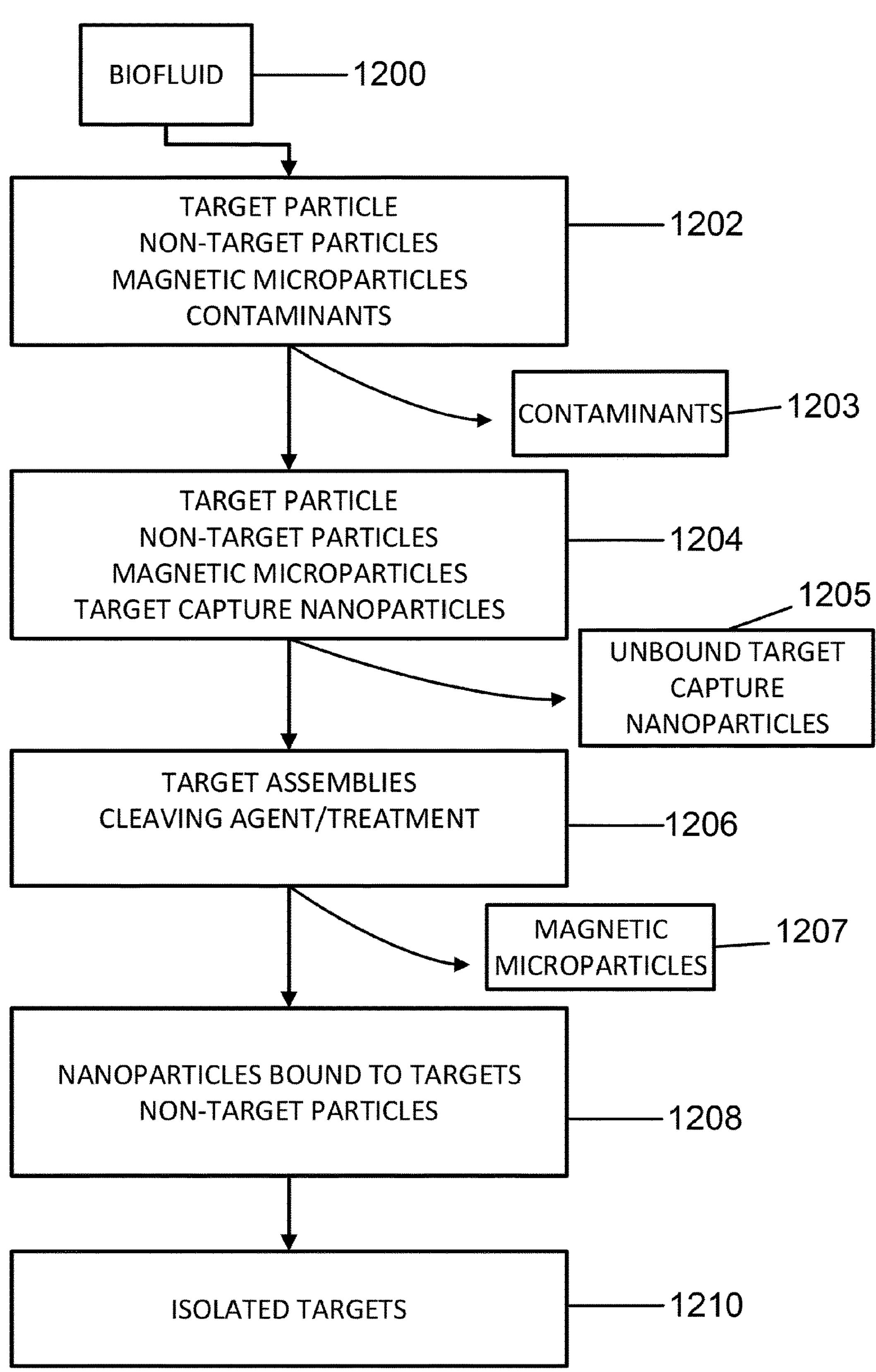
FIG. 12 illustrates a model system for carrying out the method steps of FIG. 10.

FIG. 12 shows a model system to carry out the steps of the any of the examples isolation methods described above. Each successive step shown can be performed in a new vessel. However, this is not necessary, and alternatively the whole method may be performed in a single vessel, where any contaminants etc. are extracted and discarded during the method. Furthermore, the method may be carried out in a single apparatus formed from a microfluidic device, in which successive compartments or chambers of the microfluidic device provide a space/volume for each step of the method. It will be understood that the target particle may be a particular type of EV e.g. an exosome.

A biofluid 1200 is obtained containing the target entity. The biofluid 1200 may be obtained from a patient or animal, or may have been obtained from a cell culture. The biofluid 1200 is introduced to a first chamber 1202 along with magnetic microparticles, which in this example act as universal capture microparticles. For example, the magnetic microparticles may be functionalised to capture all EVs, or all exosomes. First container 1202 defines a precursor mixture, where contaminants are still present.

Assemblies as seen in FIGS. 1*a*, 2*a*, and 3*a* form in this precursor mixture 1202. Once the assemblies are formed, a magnetic field is applied to the precursor 1202 in order to extract the assemblies from the rest of the mixture, including the contaminants of the biofluid 1200. The contaminants 1203 are thus separated from the mixture and are discarded.

A cleaned mixture 1204 is formed after magnetic extraction of the microparticles assemblies, and the contaminants 1203 have thus been separated from the biofluid. A plurality of target capture nanoparticles, which may be gold nanoparticles (GNPs), are added to the clean solution. The nanoparticles are functionalised such that they bind only to the target particles on the microparticles assemblies. After addition of the target capture nanoparticles, assemblies as shown in FIGS. 1*b*, 2*b*, and 3*b* are formed in the cleaned mixture 1204.

Prior to cleaving the linkers on the assemblies, mixture 1204 is treated again (in accordance with step S106) to remove any unbound target capture nanoparticles 1205, which are discarded.

The cleaned mixture 1204 is then treated in order to cleave the linkers attaching the target and non-target particles to the magnetic microparticles. Thus, a mixture with a new composition is formed in 1206 after the cleaving. It will be understood that 1204 and 1206 may be the same vessel/container, where the cleaving comprises merely exposing the cleaned solution 1204 to UV or near-UV light (in accordance with FIG. 1), in which case no agent is added. Consistent with FIG. 2, a nuclease cleaving agent may be added in mixture 1206. The constituents of mixture 1206 are illustrated according to the examples in FIGS. 1*c* and 2*c*.

A second magnetic field is applied in order to extract the now-unbound magnetic microparticles 1207 from the mixture 1206. The result of extracting the microparticles is a mixture containing unbound non-target particles, and target particles bound to the target capture nanoparticles. Either dielectrophoresis or centrifugation is applied to mixture 1208 in order to extract the nanoparticles and thus isolate the targets 1210. For example, the bound nanoparticle-target assemblies may be attracted to an electrode array consistent with FIG. 7, allowing the unbound non-target particles to be washed away. The result is thus a mixture containing only the target particles and the nanoparticles. In accordance with steps S200 onwards of FIG. 11, the nanoparticles can be cleaved away from the targets, for further downstream applications, e.g., quantification, sensing, characterisation, and so forth, of the targets and their biological contents.

Exosome Characterization

Figure 13:
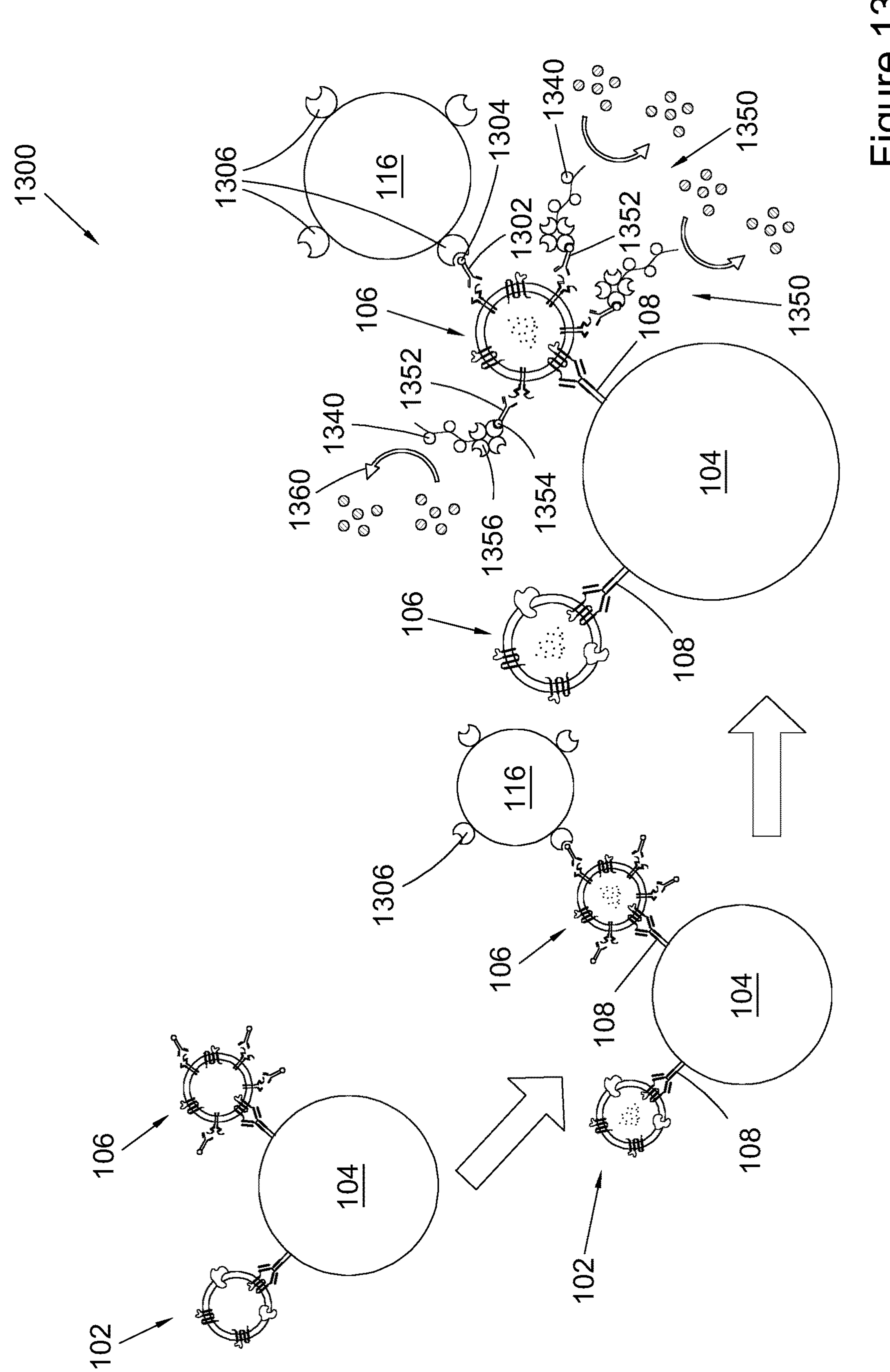
FIG. 13 illustrates an example method of determining a number of binding sites on an extracellular vesicle.

Referring to FIG. 13, there is now described a method 1300 of determining a number of binding sites, such as epitopes, on an extracellular vesicle such as an exosome.

A corresponding system may be configured to perform the method e.g. by using a computing system with sensor interfaces for sensing the electrical response of the liquid sample and for interrogating the reporters e.g. using one or more optical sensors. The computing system may be configured to perform the method by providing processor control code and/or dedicated or programmed hardware e.g. electronic circuitry to communicate with the sensor interfaces to implement the method.

The method may comprise obtaining a liquid sample containing extracellular vesicles 102, 106, for example using a magnetic bead-based technique as described above. The liquid sample may originate from a biofluid such as an excreted biofluid, a secreted biofluid, a biofluid obtained with a needle, or a biofluid which results from a pathological process such as a blister or cyst.

The method may further comprise attaching electrically conducting, e.g. gold nanoparticles 116 to the extracellular vesicles.

In implementations an average dimension of the conducting nanoparticles is larger than an average dimension of the extracellular vesicles. With this limitation steric hindrance results in around one nanoparticle being attached to each EV, or i.e. on average around a 1:1 or 1:2 ratio. However a substantially 1:1 ratio may be ensured by the use of magnetic beads 104 as described below.

In some implementations the nanoparticles may have a minimum dimension of around 100 nm, 150 nm or 200 nm; the extracellular vesicles may have a maximum dimension of less than 200 nm, 150 nm or 100 nm e.g. in the range 50 nm 150 nm.

The nanoparticles may be attached to the extracellular vesicles in any convenient manner, for example by attaching an antibody 1302 to the nanoparticle which binds to a surface protein of a target extracellular vesicle, e.g. to a generic or specific epitope target. For example the antibody may be conjugated to a biotin molecule 1304 and attached to the nanoparticle by via a biotin-binding protein 1306 such as an avidin e.g. streptavidin. Streptavidin-modified gold nanoparticles are available off the shelf.

Thus the method may comprise obtaining conducting nanoparticles, e.g. with a biotin-binding protein, and with a first binding site recognition element e.g. linked to biotin and linked by the biotin to the biotin-binding protein.

The method may limit a number of electrically conducting nanoparticles attached to each extracellular vesicle, e.g. to obtain a 1:1 ratio where, for a majority of the EVs, each EV has just one nanoparticle attached. This may be achieved by attaching magnetic beads 104 to extracellular vesicles in the liquid sample, where the magnetic beads have an (average) maximum dimension which is larger than the (average) maximum dimension of the electrically conducting nanoparticles. In some implementations the (average) maximum dimension of the magnetic beads is at least 2×, 5× or 10× as large as the (average) maximum dimension of the electrically conducting nanoparticles (as shown in FIG. 5).

The size difference substantially ensures that just one electrically conducting nanoparticle is able to attach to each EV. Thus the method may further comprise attaching the electrically conducting nanoparticles to the extracellular vesicles whilst the magnetic beads are attached.

In some implementations the magnetic beads are configured to selectively attach to EVs as opposed to other components of the liquid sample, e.g. using a generic antibody 108 as previously described. A magnetic separation technique may then be used to separate the EVs from other materials in the liquid sample, to prepare a purified liquid sample for determining the number of binding sites on the EVs. Optionally, however, the magnetic beads may selectively attach to particular binding targets on the EVs, to select target EVs.

In some other implementations the magnetic beads are selectively attached for selecting a subset of the EVs i.e. target EVs. The method may then comprise processing the liquid sample, e.g. using a magnetic field, to select extracellular vesicles with magnetic beads attached to obtain a purified liquid sample containing target extracellular vesicles.

In implementations the magnetic beads are detached from the selected extracellular vesicles before sensing the electrical response e.g. by cleaving a disulphide bond or photocleavable linker as described in the background above. Reporters, described below, may be attached before or after detaching the magnetic beads.

In some implementations, e.g. where a generic attachment to EVs is used, the electrically conducting nanoparticles, and the reporters described below may selectively attach to particular binding sites on the EVs. Then the EVs with attached electrically conducting nanoparticles, i.e. the target EVs, may be separated from a remainder of the EVs e.g. by dielectrophoresis. In implementations this is done after detaching the magnetic beads.

Implementations of the method include attaching reporters 1340 to binding sites on the extracellular vesicles. A reporter, e.g. to target epitopes on EVs, may be a molecule or molecular system which has detectable response e.g. an optical or chemical response 1360 when triggered or bound. The reporter may include an enzyme such as HRP (horseradish peroxidase) or a fluorophore, such as Alexa Fluor 488 dye, conjugated to an antibody.

A reporter may also include a molecular system where e.g., the antibody receptor to the target epitopes on EVs is linked to moieties that enable linkage to a reporter molecule. One example is the biotin-streptavidin system. Biotin can be conjugated to the recognition antibodies, and streptavidin conjugated to HRP or Alexa Fluor 488, so that ultimately the reporter antibodies are linked to the reporter molecules. This has advantages over the direct linkage of an antibody to a reporter because the binding of biotin to streptavidin is one of the strongest non-covalent interactions, and because signal amplification cascades can be triggered.

Thus, as previously described, the method may comprise providing a detection system comprising a second binding site recognition element. The second binding site recognition element may be linked to biotin and a biotin-binding protein may be attached to the reporter. The second binding site recognition element may comprise an antibody, which may be, but is not necessarily, the same antibody as the first binding site recognition element.

In general the response may be e.g. colorimetric, in the presence of a suitable substrate (e.g. TMB for HRP) or fluorescent (e.g. excitation/emission at specific wavelengths) or chemiluminescent (emission of light as the result of a chemical reaction). For example, a reporter may only exhibit such an optical response when it binds, directly or indirectly, to a target. The reporter may need additional treatment to exhibit the response e.g. treatment with a reagent such as a colour-developing reagent or promoter. In some systems the response may include a change in turbidity e.g. due to precipitation.

In general the reporters are molecular scale, i.e. comprise molecules or systems of molecules, and are therefore not subject to the same steric hindrance as the nanoparticles. Thus multiple, e.g. >2, reporters may bind to a single extracellular vesicle.

In some implementations a detection system 1350 comprises an antibody 1352 linked to biotin 1354; and a biotin-binding protein 1356 such as avidin or streptavidin attached e.g. conjugated to the reporter 1340 (optionally via a second antibody). Attaching reporters to the binding sites may comprise allowing the liquid sample containing the extracellular vesicles to interact with the detection system. The antibody and reporter may be applied sequentially or together. In some implementations the detection system may comprise multiple different antibodies each linked to biotin.

In some implementations, but not necessarily, the antibody attached to the nanoparticle (e.g. via a biotin-streptavidin link) and the antibody of the detection system are the same antibody. Where the antibody is the same the nanoparticles and reporters may more easily be bound in a single step, but in principle any antibody may bind to the reporters and compete with the binding to the nanoparticles. It is beneficial if the reporters are strongly bound, to avoid loss of reporters.

In some implementations the method may instead be used, for example, to determine a number of EVs that have a first binding target e.g. a first antigen but the reporters may be attached to a second, different binding target e.g. to measure the biomarker concentration of another biomarker.

In some implementations a signal from the reporters may be amplified, as described in more detail later. Thus attaching reporters to binding sites on the extracellular vesicles may comprise attaching smaller nanoparticles to the extracellular vesicles. The nanoparticles may have an average (maximum) dimension that is smaller than an average (maximum) dimension of the extracellular vesicles. The reporters may then be attached to the smaller nanoparticles.

The method/system then interrogates the reporters to determine a total number of bindings of the reporters to the extracellular vesicles. For example the reporters may be coloured or fluorescent reporters and the method/system may measure an optical response of the liquid sample such as a colour, fluorescence or chemiluminescence. More specifically the method/system may determine an absorbance, transmittance, or reflectance, at one or more wavelengths, or an intensity of fluorescence or chemiluminescence. In this context a coloured, fluorescent or chemiluminescence reporter may be a reporter which needs a colour-developing reagent or promoter to report a response. In some systems a concentration of reporters in liquid sample may be determined. The total number of bindings may be determined from the optical (or other) response e.g. based on an initial calibration process or calculated directly. The determination of the total number of bindings may be approximate, and may be for a defined volume of the liquid sample.

The method/system also determines a number of extracellular vesicles in the liquid sample by sensing an electrical response of the liquid sample, e.g. as described above with reference to FIG. 9.

The determination of the total number of extracellular vesicles may be approximate, and may be for a defined volume of the liquid sample. In implementations the electrical response of the liquid sample is sensed using a pair of electrodes spaced apart by a distance which is of a similar magnitude to a maximum dimension of a nanoparticle. This is so that, in implementations, the electrodes may be spanned by a single nanoparticle (although spanning by e.g. 2 nanoparticles may suffice in some applications). For example the electrodes may be separated by a lateral distance of less than 200 nm, 100 nm, 50 nm or 20 nm. Various techniques for the fabrication of such electrodes are described in the literature; purely by way of example, e.g. in Serdio et al., *Nanoscale,* 2012, 4, 7161.

The sensed electrical response may be a magnitude of current flowing between the electrodes when a voltage is applied to the electrodes, e.g. as previously described. Conveniently a DC voltage is applied and a DC current sensed; however in some implementations an AC voltage may be applied. The electrical response may be sensed directly, via the electrodes, or in principle indirectly e.g. by remotely sensing an RF (radio frequency) response of the system. A magnitude of the applied voltage may be less than 20 volts or less than 10 volts.

The method/system may be calibrated to enable a number of electrically conducting nanoparticles spanning the electrodes to be determined. In some implementations step changes in current may be seen according to the number of nanoparticles across the electrodes; also or instead a number of nanoparticles across the electrodes may be visualised using a scanning electron microscope. Without wishing to be bound by theory, the nanoparticles appear to connect, and may fuse, to the electrodes when a voltage is applied, which assists a flow of current.

The electrical response is dependent upon the number of nanoparticles e.g. the current depends on the number of nanoparticles spanning the electrodes. However because in implementations the nanoparticles are at least as big as the target EV, and the target EV is already immobilized on a large magnetic particle, an approximate 1:1 ratio between the number of nanoparticles and the number of target EVs can be assumed. Thus the number of conducting nanoparticles spanning the electrodes is a measure of the number of target EVs in the liquid sample. In some implementations the number of conducting nanoparticles spanning the electrodes is taken to be the same as the number of target EVs in the liquid sample. This assumption is strengthened if the nanoparticles are focussed onto the electrodes e.g. by dielectrophoresis, e.g. by applying an AC voltage to the electrodes. Also or instead a calibration factor may be applied.

Once values have been determined for i) for the estimated total number of bindings and ii) the estimated number of extracellular vesicles these may be combined to estimate the number of binding sites or epitopes per extracellular vesicle, more specifically the number of binding sites to which the reporter (antibody) binds. The estimates may be combined by dividing total number of bindings by the number of extracellular vesicles, optionally adding one (or two) to the total number of bindings to compensate for the site at which the nanoparticle is bound; or a more sophisticated approach based on calibration curves may be used.

The number of binding sites or epitopes per extracellular vesicle can vary considerably but may be of order 1-10000.

In some implementations the number of several different of epitope biomarkers may be investigated at the same time, e.g. by carefully selecting fluorophores with different wavelengths and sensing the signals with one or more photodetectors. For example the extracellular vesicle is bound to a conducting nanoparticle via an antibody, and different additional antibodies functionalized with fluorophores may be added. The extracellular vesicles can then be attracted to the electrodes via the nanoparticles, to count the number of extracellular vesicles and responses of the different of epitope biomarkers measured e.g. by measuring at different wavelengths and analysing the responses.

Figure 14:
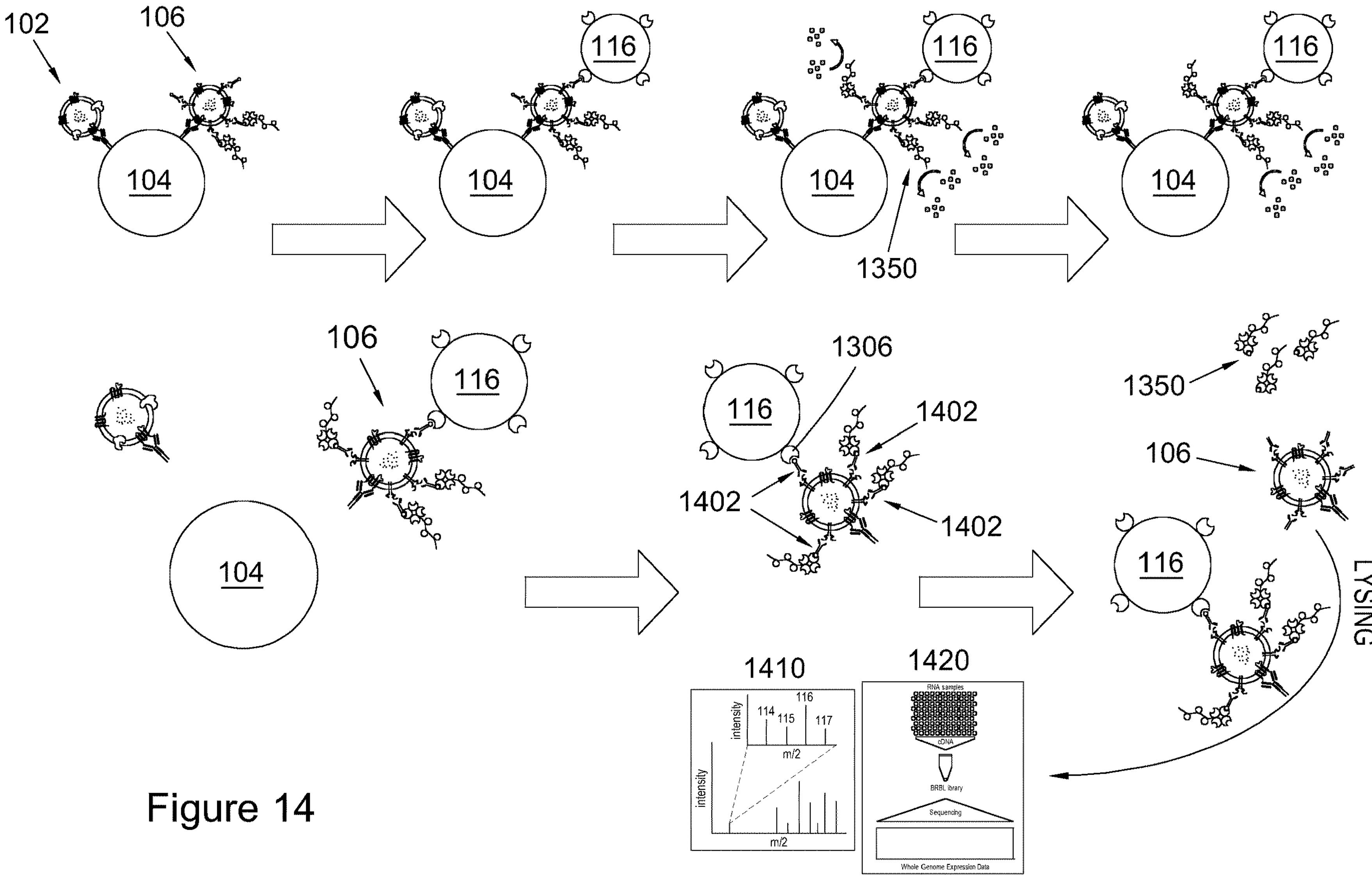
FIG. 14 illustrates the method of FIG. 13 including a preparation step for further analysis.

FIG. 14 illustrates an overview of an example of the above described process, illustrating preparation for an optional additional step of analysing surface biomarkers or binding sites and/or contents of the EVs. Thus, after the EVs have been attached to the magnetic beads, e.g. in a well of a multiwell plate, (gold) nanoparticles are attached to the target EVs in a 1:1 ratio and surplus nanoparticles washed away. Then reporters are attached and used to detect a number of epitopes, e.g. using a colour change such as a change of TMB (3,3',5,5'-tetramethylbenzidine) from a colourless form to an oxidised, coloured form driven by the HRP (horseradish peroxidase) enzyme or using fluorophores and measuring the emission at one or more specific wavelengths upon light excitation. The magnetic beads, and in implementation non-target EVs, may then be cleaved e.g. using photo- or thermal-cleaving, and washed away. Detection of the electrical response may be performed before or after cleaving e.g. optical cleaving of the nanoparticles from the target EVs since the sensed electrical current is due to the electrically conducting e.g. gold nanoparticles. In implementations the nanoparticles may be attracted to and concentrated around the electrodes, e.g. by DEP or other flow-based techniques. Triggering of the reporter molecule, e.g. HRP or a fluorophore, can occur either before or after the nanoparticle is attracted to electrodes, and before or after the nanoparticles and target EVs have been cleaved. Optionally, after the nanoparticles and target EVs have been cleaved from one another the target EVs may be lysed for biomarker fingerprinting e.g. by means of mass spectrometry and/or RNA or DNA sequencing techniques.

Thus in some implementations the method/system may detach the extracellular vesicles from one or both of the electrically conducting nanoparticles and the reporters. For example this may involve cleaving a connection 1402 between the antibody and the biotin molecule attached to it (linking to the nanoparticle/reporter) e.g. by chemically cleaving a disulphide bond. Cleaveable biotinylation reagents are available off the shelf.

Optionally the method/system may then separate the extracellular vesicles from the electrically conducting nanoparticles, e.g. by centrifugation or other means, and the extracellular vesicles may be lysed and their contents characterized e.g. by DNA or RNA sequencing, mass spectrometry (MS), gas chromatography (GC), GC-MS, microscopy, spectroscopy, screening, or using other ways of fingerprinting, as also described earlier. For example, item 1410 shows target exosome protein cargo sequencing using (liquid chromatography) mass spectrometry. As another example item 1420 shows target exosome RNA cargo sequencing using RNA-Seq (next generation sequencing). In the illustrated example whole genome expression data may be used to generate a BRB (Bulk RNA Barcoding) library e.g. using Illumina sequencing, that is used to produce cDNA and thence RNA samples. An advantage of combining the previously described techniques with MS or sequencing analysis is that implementations of the method allow quantification of the number of target EVs sent for analysis.

In some implementations of the method the binding sites are epitopes of an exosome e.g. a tumour exosome. In general the number of binding sites is of diagnostic value e.g. for tumour, e.g. breast tumour, identification/characterization.

In a variant of the above described method/system, there is no compensation for the number of extracellular vesicles.

Figure 15:
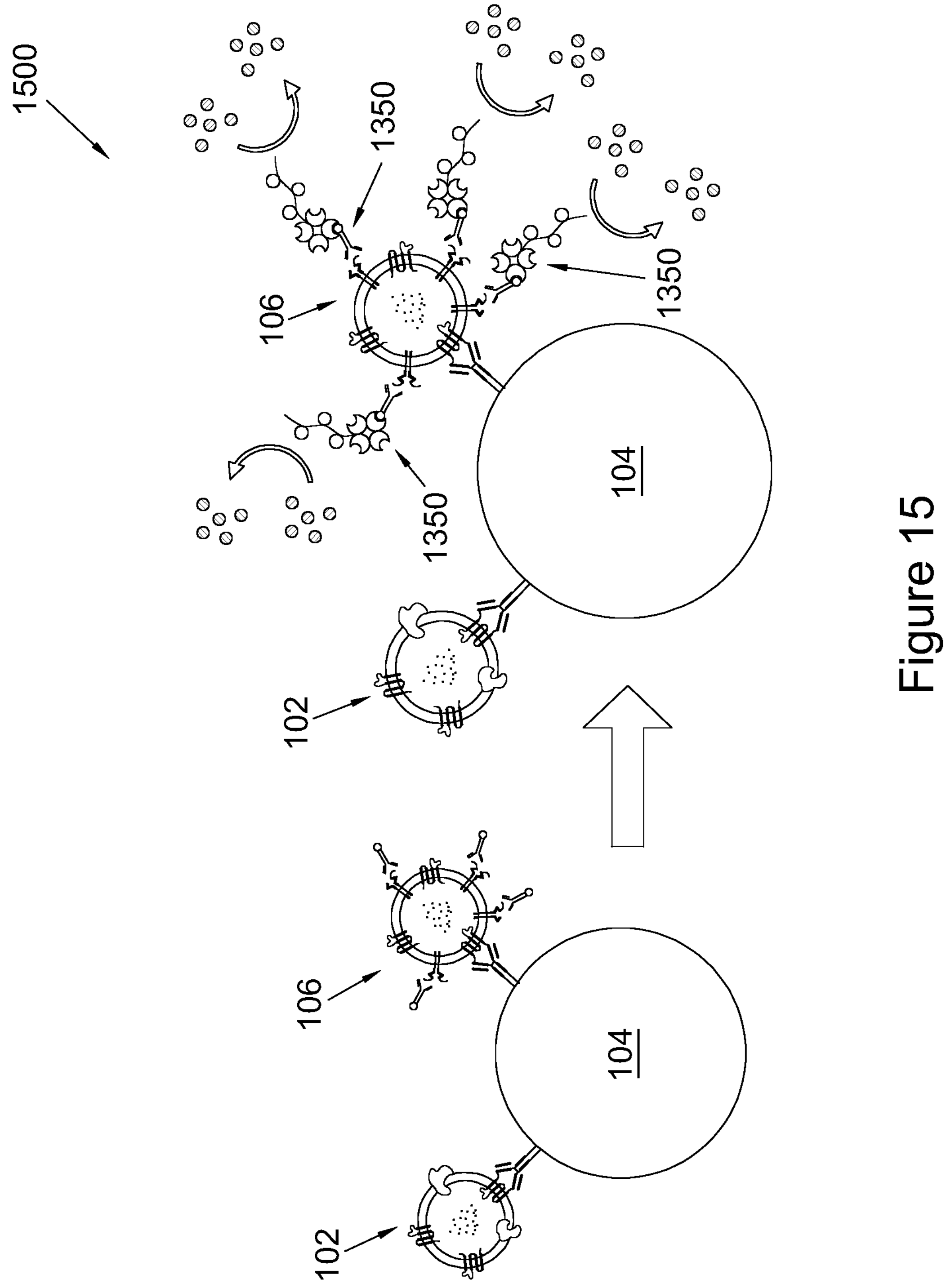
FIG. 15 illustrates an example method of detecting binding sites on an extracellular vesicle.

Thus referring to FIG. 15, there is now described a method 1500 of detecting binding sites, e.g. epitopes, on an extracellular vesicle. The method may comprise obtaining a liquid sample containing extracellular vesicles, and attaching reporters to binding sites on the extracellular vesicles. Attaching the reporters may comprise providing a detection system comprising an antibody linked to biotin and a biotin-binding protein attached to the reporter and allowing the liquid sample containing the extracellular vesicles to interact with the detection system. The reporters may then be optically interrogated to characterize a number of bindings of the reporters to the extracellular vesicles.

Even without knowing the number of extracellular vesicles in the liquid sample (or EV density) such an approach may still provide an approximate characterization of the number of binding sites detected. Also or instead the method may be used to determine relative numbers of binding sites in two different liquid samples, e.g. from two different patients, or from a patient and a healthy person, or from the same patient at two different times. Also or instead the method may be used to determine relative numbers of two different types of binding site in the same liquid sample, e.g. as selected by different antibodies.

In some approaches this method may be used to detect epitopes, e.g. of a particular type, and then the previously described method may be used to quantify the epitopes.

One difficulty that can arise is that a large number of epitopes may be needed for a detectable signal; and/or a target EV may only be present at very low concentration. In implementations therefore the liquid sample is treated to amplify the optical response.

Figure 16:
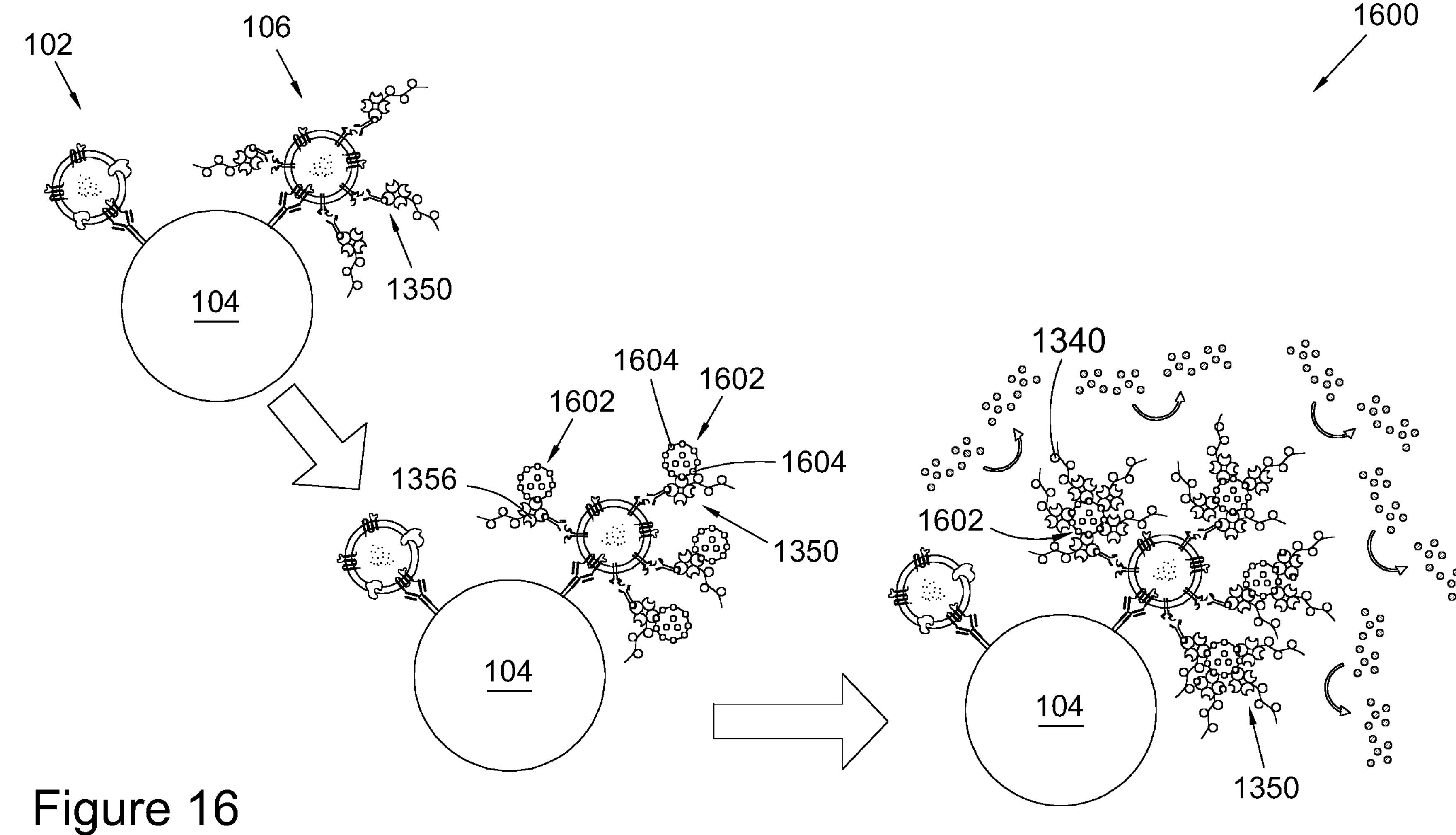
FIG. 16 illustrates a signal amplification process.

FIG. 16 illustrates an amplification process 1600. Referring to FIG. 16, in some implementations the amplification of the optical response may be performed by attaching nanoparticles 1602 functionalised, e.g. with biotin molecules 1604, to the extracellular vesicles. For example, but not essentially, a nanoparticle 1602 may be attached to one of the "spare" binding sites on a reporter/detection system including a tetrameric biotin-binding protein, as illustrated. Conveniently the nanoparticles comprise gold but the nanoparticles do not need to electrically conduct.

In implementations an average dimension of the conducting nanoparticles is smaller than an average maximum dimension of the extracellular vesicles to reduce steric hindrance, in particular to enable multiple nanoparticles to be attached to a single EV. For example such nanoparticles may have an (average) maximum dimension, e.g. diameter, of less than 150 nm, 100 nm, 50 nm, 20 nm or 10 nm. Depending on the density of binding sites there may be a nanoparticle attached to each of a majority of or substantially all of the binding sites i.e. in implementations, one nanoparticle per binding site.

The amplification may then further comprise allowing the liquid sample containing the extracellular vesicles to interact with the detection system and in particular the nanoparticles, such that each nanoparticle 1502 links to multiple reporters/detection systems 1340/1350. More particularly one biotin-binding protein molecule links the antibody linked to biotin with one of the nanoparticles functionalised with biotin molecules which in turn links to multiple biotin-binding protein molecules each attached to a respective reporter. In this way multiple reporters may be attached to each binding site, amplifying a detection signal from the reporters indicating presence (and to some extent number) of the binding sites. Although the technique is convenient when used with optical reporters it may also be used with other types of reporter.

This type of signal amplification may also be used with the previously described method of quantifying a number of binding sites on an extracellular vesicle. For example, after the electrically conducting nanoparticles have been attached to the extracellular vesicles a second set of smaller nanoparticles (less than a size of the EV) may be attached to the EVs as part of the step of attaching the reporters to binding sites on the extracellular vesicles. In this approach the reporters are indirectly attached to the binding sites.

Once binding sites have been detected/quantified as described above contents of the EVs may again be characterized as previously described.

In some implementations of this variant method, a magnetic separation technique may be used to purify the liquid sample and/or to select target EVs prior to detecting epitopes. Thus again magnetic beads may be selectively attached to EVs (as opposed to other components of the liquid sample), or to specific target EVs, and the liquid sample processed to purify the attached components. The magnetic beads may be detached before attaching the smaller nanoparticles.

Features of the method and system which have been described or depicted herein in combination e.g. in an embodiment, may be implemented separately or in sub-combinations. Features from different embodiments may be combined. Thus each feature disclosed or illustrated in the present specification may be incorporated in the invention, whether alone or in any appropriate combination with any other feature disclosed or illustrated herein. Method steps should not be taken as requiring a particular order e.g. that in which they are described or depicted, unless this is specifically stated. A system may be configured to perform a task by providing processor control code and/or dedicated or programmed hardware e.g. electronic circuitry to implement the task.

Aspects of the method and system have been described in terms of embodiments but these embodiments are illustrative only and the claims are not limited to those embodiments. Those skilled in the art will be able to make modifications and identify alternatives in view of the disclosure which are contemplated as falling within the scope of the claims.

The invention claimed is:

1. A method of detecting binding sites on an extracellular vesicle, comprising:

obtaining a liquid sample containing extracellular vesicles;

attaching reporters to binding sites on the extracellular vesicles; and optically interrogating the reporters to characterize a number of bindings of the reporters to the extracellular vesicles; and wherein attaching reporters to binding sites on the extracellular vesicles comprises:

providing a detection system comprising a binding site recognition element linked to biotin and a biotin-binding protein attached to the reporter; and allowing the liquid sample containing the extracellular vesicles to interact with the detection system.

2. The method of claim 1 further comprising treating the liquid sample to amplify the optical response.

3. The method of claim 2 wherein treating the liquid sample to amplify the optical response comprises:

attaching nanoparticles to the extracellular vesicles, wherein the nanoparticles are functionalised with biotin molecules;

allowing the liquid sample containing the extracellular vesicles to interact with the detection system and the nanoparticles such that one biotin-binding protein molecule links the antibody linked to biotin with one of the nanoparticles functionalised with biotin molecules which in turn links to multiple biotin-binding protein molecules each attached to a respective reporter.

4. The method of claim 3 wherein an average dimension of the nanoparticles is smaller than an average dimension of the extracellular vesicles.

5. The method of claim 1, further comprising attaching the extracellular vesicles to magnetic beads.

6. The method of claim 5, wherein magnetic beads are functionalised with one or more of surface-bound binding agents, antibodies, a photo-cleavable linker, a disulfide bridge, DNA, RNA, or DNA-RNA hybrid.

7. The method of claim 1, wherein attaching reporters to binding sites comprises:

attaching a first reporter to a first binding site; and attaching a second reporter to a second binding site, wherein the first and second reports exhibit a different optical response, and optionally wherein the different optical response comprises the first and second reporters providing optical responses at different wavelengths.

8. The method of claim 7, wherein the detection system comprises a second binding site recognition element linked to biotin and a biotin-binding protein attached to the second reporter, wherein the second binding site recognition element is different to the first binding site recognition element.

9. The method of claim 1, wherein attaching reporters to binding sites on the extracellular vesicles comprises:

attaching nanoparticles to the extracellular vesicles, wherein an average dimension of the nanoparticles is smaller than an average dimension of the extracellular vesicles, and attaching the reporters to the nanoparticles.

10. The method of claim 1, wherein the reporter comprises either:

(i) an enzyme, wherein the comprises horseradish peroxidase (HRP), or (ii) a fluorophore, wherein the fluorophore comprises Alexa Fluor 488.

11. The method of claim 1, wherein the binding site recognition element is an antibody, aptamer, or lipid-binding protein.

12. The method of claim 1, wherein the binding sites comprise an epitope, membrane lipid or a membrane bound protein.

13. The method of claim 1, further comprising determining, based on the number of bindings of the reporters, at least one of:

a concentration of the reporters;

a concentration of extracellular vesicles;

the concentration of extracellular vesicle proteins; or the concentration of extracellular vesicle lipids.

14. The method of claim 1, wherein the extracellular vesicle comprises one or more surface markers, optionally wherein the one or more surface markers comprise tetraspanin, and further optionally wherein the tetraspanin comprises one or more of CD9, CD63, CD81, CD326, CD82, CD37 or CD41.

15. The method of claim 1, wherein the reporters comprise enzymatic, chemiluminescent, or fluorescent reporters, and wherein optically interrogating the reporters comprises measuring an optical response of the liquid sample.

16. The method of claim 1, further comprising, prior to optically interrogating the reporters, treating the reporters with a reagent.

17. The method of claim 1, wherein optically interrogating the reporters comprises measuring an optical characteristic of the reporters, wherein the optical characteristic is an absorbance, a transmittance, a reflectance or an intensity of fluorescence or chemiluminescence.

18. The method of claim 1, further comprising determining, based on the number of bindings of the reporters, an indication of at least one of a liver disease, breast cancer or a neurological disease, wherein the neurological disease is Alzheimer's disease.

19. A method of determining a number of binding sites on an extracellular vesicle, comprising:

obtaining a liquid sample containing extracellular vesicles;

attaching electrically conducting nanoparticles to the extracellular vesicles;

attaching reporters to binding sites on the extracellular vesicles;

interrogating the reporters to determine a total number of bindings of the reporters to the extracellular vesicles;

determining a number of extracellular vesicles in the liquid sample by sensing an electrical response of the liquid sample using a pair of electrodes separated by less than an average maximum dimension of the electrically conducting nanoparticles; and combining the determined total number of bindings and the determined number of extracellular vesicles in the liquid sample to determine a number of binding sites per extracellular vesicle.

20. The method as claimed in claim 19 further comprising limiting a number of electrically conducting nanoparticles attached to each extracellular vesicle by:

selectively attaching the extracellular vesicles to magnetic beads in the liquid sample, wherein the magnetic beads have an average maximum dimension which is larger than the average maximum dimension of the electrically conducting nanoparticles;

processing the liquid sample to select magnetic beads with extracellular vesicles attached to obtain the liquid sample containing extracellular vesicles;

attaching the electrically conducting nanoparticles to the extracellular vesicles whilst attached to the magnetic beads; and detaching the magnetic beads from the selected extracellular vesicles before sensing the electrical response.

21. The method as claimed in claim 19 wherein an average dimension of the conducting nanoparticles is larger than an average dimension of the extracellular vesicles.

22. The method as claimed in claim 19, wherein attaching conducting nanoparticles to the extracellular vesicles comprises:

obtaining conducting nanoparticles with a biotin-binding protein and a first binding site recognition element linked to biotin, and linked by the biotin to the biotin-binding protein; and allowing the liquid sample containing the extracellular vesicles to interact with the conducting nanoparticles.

23. The method as claimed in claim 19, wherein attaching reporters to binding sites on the extracellular vesicles comprises at least one of:

(i) providing a detection system comprising a second binding site recognition element linked to biotin and a biotin-binding protein attached to the reporter; and allowing the liquid sample containing the extracellular vesicles to interact with the detection system;

(ii) attaching first reporters to first binding sites on the extracellular vesicles and second reporters to second binding sites on the extracellular vesicles, wherein interrogating the reporters to determine a total number of bindings of the reporters to the extracellular vesicles comprises interrogating the first reporters to determine a total number of bindings of the first reporters and interrogating the second reporters to determine a total number of bindings of the second reporters, and wherein the method comprises determining a number of binding sites per extracellular vesicle for each of the first binding sites and the second binding sites; and iii) attaching smaller nanoparticles to the extracellular vesicles, wherein the smaller nanoparticles have an average dimension smaller than an average dimension of the extracellular vesicles, and attaching the reporters to the smaller nanoparticles.

24. The method as claimed in claim 19, wherein:

attaching conducting nanoparticles to the extracellular vesicles comprises:

obtaining conducting nanoparticles with a biotin-binding protein and a first binding site recognition element linked to biotin, and linked by the biotin to the biotin-binding protein; and allowing the liquid sample containing the extracellular vesicles to interact with the conducting nanoparticles; and attaching reporters to binding sites on the extracellular vesicles comprises:

providing a detection system comprising a second binding site recognition element linked to biotin and a biotin-binding protein attached to the reporter; and allowing the liquid sample containing the extracellular vesicles to interact with the detection system;

the method comprising attaching the conducting nanoparticles then attaching the reporters.

25. The method as claimed in claim 19, wherein sensing the electrical response of the liquid sample comprises at least one of:

(i) measuring an electrical current flowing between the electrodes; and (ii) concentrating the electrically conducting nanoparticles in a vicinity of the electrodes using dielectrophoresis.

26. The method as claimed in claim 19, wherein the reporters comprise enzymatic, chemiluminescent, or fluorescent reporters, and wherein interrogating the reporters comprises measuring an optical response of the liquid sample.

27. The method as claimed in claim 19, further comprising detaching the extracellular vesicles from the electrically conducting nanoparticles and/or from the reporters, separating the extracellular vesicles from the electrically conducting nanoparticles, and characterizing contents of the extracellular vesicles.

28. The method as claimed in claim 19, wherein the extracellular vesicles are exosomes and the binding sites are epitopes.

29. The method of detecting a disease in a biofluid sample from a patient using the method of claim 19, comprising obtaining the liquid sample containing extracellular vesicles from the biofluid sample.

30. A system for detecting binding sites on an extracellular vesicle, wherein the system is configured to:

accept a liquid sample containing extracellular vesicles;

attach reporters to binding sites on the extracellular vesicles; and optically interrogate the reporters to characterize a number of bindings of the reporters to the extracellular vesicles; and wherein attaching reporters to binding sites on the extracellular vesicles comprises:

providing a detection system comprising a binding site recognition element linked to biotin and a biotin-binding protein attached to the reporter; and allowing the liquid sample containing the extracellular vesicles to interact with the detection system.

31. The system of claim 30, comprising one or more optical sensors for optically interrogating the reporters.

32. The system of claim 30, wherein the system is configured to attach the extracellular vesicles to magnetic beads.

33. A system for determining a number of binding sites on an extracellular vesicle, wherein the system is configured to:

accept a liquid sample containing extracellular vesicles;

attach electrically conducting nanoparticles to the extracellular vesicles;

attach reporters to binding sites on the extracellular vesicles;

interrogate the reporters to determine a total number of bindings of the reporters to the extracellular vesicles;

determine a number of extracellular vesicles in the liquid sample by sensing an electrical response of the liquid sample using a pair of electrodes separated by less than an average maximum dimension of the electrically conducting nanoparticles; and combine the determined total number of bindings and the determined number of extracellular vesicles in the liquid sample to determine number of binding sites per extracellular vesicle.

34. The system of claim 33 further configured to attach the extracellular vesicles to magnetic beads in the liquid sample before attaching the conducting nanoparticles to the extracellular vesicles.

* * * * *